US012606585B2

(12) United States Patent
Pijnenborg et al.

(10) Patent No.: US 12,606,585 B2
(45) Date of Patent: Apr. 21, 2026

(54) FLUORINATED HEXOSES

(71) Applicant: Stichting Radboud Universiteit, Nijmegen (NL)

(72) Inventors: Johan Franciscus Adrianus Pijnenborg, Nijmegen (NL); Thomas Jan Boltje, Doorn (NL); Emiel Rossing, Nijmegen (NL)

(73) Assignee: Stichting Radboud Universiteit

( * ) Notice: Subject to any disclaimer, the term of this patent is extended or adjusted under 35 U.S.C. 154(b) by 421 days.

(21) Appl. No.: 18/044,384

(22) PCT Filed: Sep. 9, 2021

(86) PCT No.: PCT/EP2021/074852

§ 371 (c)(1),
(2) Date: Mar. 8, 2023

(87) PCT Pub. No.: WO2022/053576

PCT Pub. Date: Mar. 17, 2022

(65) Prior Publication Data

US 2023/0340002 A1 Oct. 26, 2023

(30) Foreign Application Priority Data

Sep. 9, 2020 (EP) .................................... 20195308

(51) Int. Cl.
*C07H 11/04* (2006.01)

(52) U.S. Cl.
CPC .................................... *C07H 11/04* (2013.01)

(58) Field of Classification Search
None
See application file for complete search history.

(56) References Cited

U.S. PATENT DOCUMENTS 5,210,078 A * 5/1993 Toyokuni ................ A61P 35/00 514/23

FOREIGN PATENT DOCUMENTS

| | | | |
|---|---|---|---|
| WO | 9219632 | A1 | 11/1992 |
| WO | 2014130613 | A2 | 8/2014 |
| WO | 2014130613 | A3 | 8/2014 |

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 202).*

Allen et al., "Facile Modulation of Antibody Fucosylation with Small Molecule Fucostatin Inhibitors and Cocrystal Structure with GDP-Mannose 4,6-Dehydratase", ACS Chemical Biology, vol. 11, No. 10, Oct. 21, 2016 (Oct. 21, 2016), pp. 2734-2743, XP055352875, ISSN: 1554-8929, DOI: 10.1021/acschembio.6b00460.

Chang et al.: "CDP-6-deoxy-6,6-difluoro-D-glucose: A Mechanism-Based Inhibitor for CDP-D-glucose 4,6-Dehydratase", Journal of the American Society, vol. 120, No. 37, Feb. 9, 1998 (Feb. 9, 1998), pp. 9698-9699, XP055773316.

Beswick et al.: "Exploring anomeric glycosylation of phosphoric acid: Optimisation and scope for non-native substrates", Carbohydrate Research, Pergamon, GB, vol. 488, Dec. 19, 2019 (Dec. 19, 2019), XP086017685, ISSN: 0008-6215, DOI: 10.1016/J.CARRES. 2019.107896 [retrieved on Dec. 19, 2019].

* cited by examiner

*Primary Examiner* — Dale R Miller
(74) *Attorney, Agent, or Firm* — Ipsilon USA—NLO

(57) ABSTRACT

The present invention relates to a new class of compounds based on a hexose featuring at least two 6-fluorides. The class is useful as inhibitors of 4,6-dehydratase enzymes. Such inhibitors are suitable for use as a medicament, for example for treating, preventing, or delaying cancer, tumor metastasis, inflammation, infections, or genetic disorders.

15 Claims, 7 Drawing Sheets

FLUORINATED HEXOSES

FIELD OF THE INVENTION

The present invention relates to a new class of compounds based on a hexose featuring at least two 6-fluorides. The class is useful as inhibitors of 4,6-dehydratase enzymes. Such inhibitors are suitable for use as a medicament, for example for treating, preventing, or delaying cancer, tumor metastasis, inflammation, infections, or genetic disorders.

BACKGROUND ART

Fucose sugars on mammalian cell membranes are essential in numerous physiological activities and play a role in pathologies like cancer, inflammation, infection, and genetic disorders. Tools to modulate fucosylation on cells are important for further elucidating fucose function and the development of potential therapeutics.

L-Fucose (Fuc) is a 6-deoxyhexose derived from L-galactose and is expressed on glycan chains that decorate cell surface proteins and lipids. The fucose residues on glycoconjugates are essential mediators of physiological and pathological activities such as tumor metastasis, inflammation, infections, and genetic disorders. It is part of the tetrasaccharide sialyl Lewisx (sLex) which is important in leukocyte recruitment and extravasation via selectin receptor binding. Aberrant expression of sLex and increased fucosylation are found in many carcinomas, promoting tumor progression. Reducing fucosylation of glycans in cancer using inhibitors of the fucose biosynthesis has therefore been recognized as a viable therapeutic option.

Glycans or proteins are fucosylated by the action of at least 13 fucosyltransferases (FucTs) that all utilize GDP-fucose as the donor substrate but differ in acceptor glycan or protein preference. Cells employ two distinct mechanisms to generate GDP-fucose, either via the recycling of fucose released during glycan turnover (salvage pathway) or via the de novo biosynthesis from mannose-1-phosphate (FIG. 1). With respect to the development of inhibitors of this process, the development of fucosyltransferase (FucT) inhibitors has attracted considerable attention (Tu, Z.; Lin, Y.-N.; Lin, C.-H., Chem. Soc. Rev. 2013, 42 (10), 4459-4475). A common strategy has been mimicking the natural substrate guanosine diphosphate fucose (GDP-Fuc).

However, the essential GDP moiety in these compounds is associated with a high polarity and low stability thereby limiting their use in vitro and in vivo by poor penetration of the cell membrane. This hurdle was recently overcome with the development of less polar, cell permeable fucose derivatives which are metabolized to the corresponding active GDP-fucose analog through the salvage pathway (Rillahan et al., Nat Chem Biol 2012, 8 (7), 661-668). These compounds target FucTs by competitive inhibition and de novo enzymes GMDS and FX by feedback inhibition (Kizuka, Y. et al., Cell Chemical Biology 2017, 24 (12), 1467-1478.e5). This strategy led to fucosylation inhibitors that are active in vitro and in vivo, showing promise in liver, breast and blood cancer models (Disis et al., Molecular Cancer Therapeutics 2020, molcanther.0500.2019). Combining a fucosylation inhibitor with immunotherapy vaccination in immunocompetent mice completely protected against tumor growth due to enhanced ADCC with LS174T colorectal carcinoma and A20 lymphoma cells (Okeley et al., Proc Natl Acad Sci USA 2013, 110 (14), 5404-5409).

However about 90% of the GDP-Fucose pool is biosynthesized via the de novo biosynthesis from GDP-mannose (Yurchenco, P. D.; Atkinson, P. H., Biochemistry 1975, 14 (14), 3107-3114). The inventors reasoned that direct inhibition of de novo fucose biosynthesis could thus be a more promising approach for inhibitor development but it remained unexplored thus far. GDP-fucose is biosynthesized from GDP-mannose by oxidation of the 4-OH and epimerization of the 3- and 5-position by GDP-mannose-4,6-dehydratase (GMDS) and subsequent reduction of the 4-ketone by GMER (FIG. 1) making these enzymes prime targets for inhibitor development.

GDP-fucose is biosynthesized from GDP-mannose by oxidation of the 4-OH and epimerization of the 3- and 5-position by GDP-D-mannose-4,6-dehydratase (GMDS, EC 4.2.1.47) and subsequent reduction of the 4-ketone by GDP-4-keto-6-deoxy-D-mannose epimerase/reductase (GMER). The GMDS and GMER enzymes are critical in the de novo biosynthesis of fucose and therefore potential targets for inhibitor development.

Similar to CDP-D-glucose-4,6-dehydratase and GDP-D-mannose-4,6-dehydratase, there are several other enzymes known with 4,6-dehydratase activity. dTDP-D-glucose-4,6-dehydratase transforms dTDP-glucose into dTDP-D-4-keto-6-deoxyglucose, which is an essential intermediate in the dTDP-L-rhamnose biosynthesis, a building block which is often structurally important to the bacterial cell wall in e.g. *Streptococcus pneumoniae* and *Escherichia coli*. Three XDP-D-N-acetylglucosamine-4,6-dehydratases are also known: PseB, LegB and PglF (Schoenhofen et al., J Biol Chem 2006, 281 (2), 723-32). LegB is a dehydratase that works on GDP-D-N-acetylglucosamine in the biosynthesis of legionaminic acid. PseB works on UDP-D-N-acetylglucosamine in the biosynthesis of pseudaminic acid. PglF works on the same substrate as PseB but in the di-N-acetylbacillosamine biosynthesis. Legionaminic acid, pseudaminic acid and bacillosamine have been identified as important virulence factors in pathogenic bacteria e.g. *Campylobacter jejuni* and *Helicobacter pylori* (Menard et al., Antimicrob Agents Chemother 2014, 58 (12), 7430-40).

There is a need for 4,6-dehydratase inhibitors with increased potency. There is a need for 4,6-dehydratase inhibitors with improved cellular uptake. There is a need for 4,6-dehydratase inhibitors with reduced molecular complexity, which are more stable, have better solubility, and are more synthetically accessible. There is a need for 4,6-dehydratase inhibitors which function via alternative mechanisms.

SUMMARY OF THE INVENTION

The inventors found that hexoses such as GDP-D-6-deoxy-difluoro-mannose (GDP-D-Rha6$F_2$) can inhibit the activity of GMDS, a 4,6-dehydratase. To allow passive diffusion over the cell membrane, lipophilic metabolic precursors were designed. To decrease e.g. fucose expression specific, non-toxic cell fucosylation inhibitors derived from mannose were invented. These molecules are metabolic prodrugs leading to intracellular formation of active inhibitors acting on GDP-Man-4,6-dehydratase (GMDS). Blocking GMDS leads to inhibition of de novo GDP-fucose biosynthesis, thereby decreasing the GDP-fucose pool. Cellular fucose expression can be inhibited up to 450 nM $EC_{50}$. Thus the invention provides a compound of general formula (1) or a salt thereof:

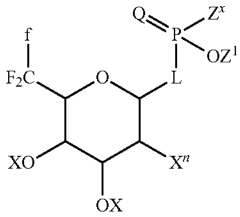

(1)

wherein f is H or F; X is in each instance independently chosen from hydrogen and a linear, branched, or cyclic C1-4acyl or alkyl wherein each carbon atom is optionally substituted by a halogen, an alkoxy, or a haloalkoxy moiety, and wherein the acyl or alkyl is optionally unsaturated; X″ is —O—X, —$NH_2$, —NH—C1-4alkyl, —N(C1-4alkyl$_2$), —NH—C1-4acyl, or —N(C1-4acyl)$_2$ wherein each carbon atom is optionally substituted by a halogen, an alkoxy, or a haloalkoxy moiety, and wherein the acyl or alkyl is optionally unsaturated; L is O, S, NH, N($CH_3$), $CH_2$, CHF, or $CF_2$; Q is O or S; $Z^x$ is $OZ^2$ or an N-linked amino acid; $Z^1$ and $Z^2$ are each independently chosen from—hydrogen,—benzyl or a linear, branched, or cyclic C1-6 acyl, alkyl, alkenyl, or alkynyl, wherein each carbon atom is optionally substituted by a halogen, an alkoxy, or a haloalkoxy moiety,—a C1-4alkyl-Q'-C1-4acyl or a C1-4alkyl-Q'-C1-4alkyl, wherein each carbon atom is optionally substituted by a halogen, an alkoxy, or a haloalkoxy moiety, and wherein Q' is O or —O—C(═O)—O— or S or —S—S—, or $Z^1$ and $Z^2$ together form a C1-4alkyl bridging moiety that is optionally substituted with halogen or a C1-7hydrocarbon, or $Z^1$ is H and $Z^2$ together with the O to which it is attached form a nucleotide. Preferably $Z^x$ is $OZ^2$ and f is F; and/or X is in each instance independently chosen from hydrogen and a linear C1-4acyl wherein each carbon atom is optionally substituted by a halogen or a methoxy moiety; and/or X″ is —O—X, —$NH_2$, or —NH—C1-4acyl; and/or L is O, S, NH, or $CF_2$; and/or Q is O; and/or $Z^1$ and $Z^2$ are each independently chosen from—hydrogen,—a linear C1-4alkyl, wherein each carbon atom is optionally substituted by a halogen, an alkoxy, or a haloalkoxy moiety,—a C1-4alkyl-O—C1-4acyl, a C1-4alkyl-O—C1-4alkyl, a C1-4alkyl-S—C1-4acyl, or a C1-4alkyl-S—C1-4alkyl, wherein each carbon atom is optionally substituted by a halogen or a methoxy moiety, or $Z^1$ and $Z^2$ together form an optionally substituted C2-3alkyl bridging moiety, or $Z^1$ is H and $Z^2$ together with the O to which it is attached form a nucleotide. In preferred embodiments f is F. Preferably L is O and preferably Q is O. In preferred embodiments X is in each instance chosen from acetyl, propionyl, and butyryl, preferably it is acetyl; and/or $Z^1$ is chosen from hydrogen, —$CH_2CH_2$—S-acetyl, and —$CH_2CH_2$—O-acetyl; and/or $Z^2$ is chosen from hydrogen, —$CH_2CH_2$—S-acetyl, and —$CH_2CH_2$—O-acetyl; or $Z^1$ and $Z^2$ together form —$CH_2$—$CH_2$— or —$CH_2$—$CH_2$—$CH_2$— or —$CH_2$—$CH_2$—CH(C5-6aryl)-. Preferably $Z^1$ and $Z^2$ represent the same moiety. The compound is preferably of general formula (1-man), (1-gluc), (1-fuc), or (1-gal):

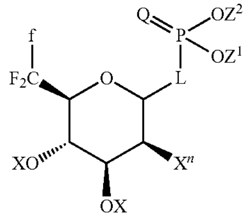

(1-man)

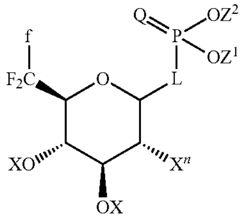

(1-gluc)

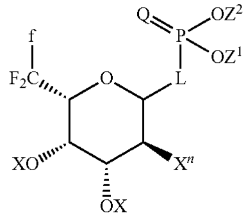

(1-fuc)

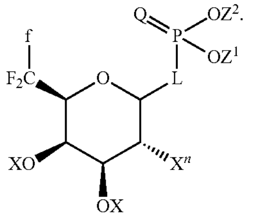

(1-gal)

More preferably it is of general formula 1-man or 1-gluc, and wherein f is F. For preferred compounds: f=H, each X is H, X″ is OH, L is O, Q is O, $Z^1$ and $Z^2$ are —$CH_2CH_2$—S-acetyl; =F, each X is H, X″ is OH, L is O, Q is O, $Z^1$ and $Z^2$ are —$CH_2CH_2$—S-acetyl; f=H, each X is acetyl, X″ is O-acetyl, L is O, Q is O, $Z^1$ and $Z^2$ are —$CH_2CH_2$—S-acetyl; f=F, each X is acetyl, X″ is O-acetyl, L is O, Q is O, $Z^1$ and $Z^2$ are —$CH_2CH_2$—S-acetyl; f=H, each X is H, X″ is OH, L is O, Q is O, $Z^1$ and $Z^2$ are H; f=F, each X is H, X″ is OH, L is O, Q is O, $Z^1$ and $Z^2$ are H; f=H, each X is acetyl, X″ is O-acetyl, L is O, Q is O, $Z^1$ and $Z^2$ are H; f=F, each X is acetyl, X″ is O-acetyl, L is O, Q is O, $Z^1$ and $Z^2$ are H; wherein preferably the compounds are of general formula 1-man.

The invention also provides such a compound for use as a medicament, wherein the medicament is preferably for use in the treatment of cancer, tumor metastasis, inflammation, infections, or genetic disorders.

The invention also provides a composition comprising a pharmaceutically acceptable excipient and a compound as defined above, preferably wherein the composition is a pharmaceutical composition. The composition is preferably for use as a medicament, wherein the medicament is preferably for use in the treatment of cancer, tumor metastasis, inflammation, infections, or genetic disorders.

The invention also provides a method for inhibiting a hexose-4,6-dehydratase, the method comprising the step of contacting the hexose-4,6-dehydratase with a compound as defined above, or with a composition as defined above. The hexose-4,6-dehydratase is preferably CDP-glucose 4,6-dehydratase, dTDP-glucose 4,6-dehydratase, GDP-mannose 4,6-dehydratase, UDP-glucose 4,6-dehydratase, UDP-N-acetylglucosamine 4,6-dehydratase, or GDP-N-acetyl-D-glucosamine 4,6-dehydratase, more preferably CDP-glucose 4,6-dehydratase, dTDP-glucose 4,6-dehydratase, GDP-mannose 4,6-dehydratase, UDP-glucose 4,6-dehydratase, or GDP-N-acetyl-D-glucosamine 4,6-dehydratase, even more preferably GDP-mannose 4,6-dehydratase, UDP-N-acetylglucosamine 4,6-dehydratase, or GDP-N-acetyl-D-glucosamine 4,6-dehydratase.

The invention also provides a method of treating, preventing, or delaying cancer, tumor metastasis, inflammation, infections, or genetic disorders in a subject in need thereof, the method comprising the step of administering to the subject an effective amount of a compound as defined above, or a composition as defined above.

DESCRIPTION OF EMBODIMENTS

Compounds

In a first aspect, the invention provides a compound of general formula (1) or a salt thereof:

(1)

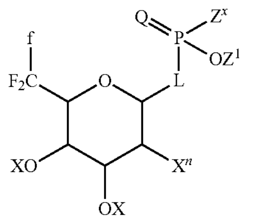

wherein f is H or F;

X is in each instance independently chosen from hydrogen and a linear, branched, or cyclic C1-4acyl or alkyl wherein each carbon atom is optionally substituted by a halogen, an alkoxy, or a haloalkoxy moiety, and wherein the acyl or alkyl is optionally unsaturated; or X″ together with the O to which it is attached forms —$NH_2$, —NH—C1-4alkyl, —N(C1-4alkyl$_2$), —NH—C1-4acyl, or —N(C1-4acyl)$_2$;

X″ is —O—X, —$NH_2$, —NH—C1-4alkyl, —N(C1-4alkyl$_2$), —NH—C1-4acyl, or —N(C1-4acyl)$_2$ wherein each carbon atom is optionally substituted by a halogen, an alkoxy, or a haloalkoxy moiety, and wherein the acyl or alkyl is optionally unsaturated;

L is O, S, NH, N($CH_3$), $CH_2$, CHF, or $CF_2$;

Q is O or S;

$Z^x$ is $OZ^2$ or an N-linked amino acid; r is preferably $OZ^2$;

$Z^1$ and $Z^2$ are each independently chosen from

- hydrogen,
- benzyl or a linear, branched, or cyclic C1-6 acyl, alkyl, alkenyl, or alkynyl, wherein each carbon atom is optionally substituted by a halogen, an alkoxy, or a haloalkoxy moiety,
- a C1-4alkyl-Q'-C1-4acyl or a C1-4alkyl-Q'-C1-4alkyl, wherein each carbon atom is optionally substituted by a halogen, an alkoxy, or a haloalkoxy moiety, and wherein Q' is O or —O—C(=O)—O— or S or —S—S—,
- or $Z^1$ and $Z^2$ together form a C1-4alkyl bridging moiety that is optionally substituted with halogen or a C1-10hydrocarbon,
- or $Z^1$ is H and $Z^2$ together with the O to which it is attached form a nucleotide.

These compounds are hexopyranoses and are referred to herein as compounds according to the invention. It is to be understood that hexoses are also encompassed by the invention. Compounds of general formula (1) are preferably of general formula (Iz).

(1z)

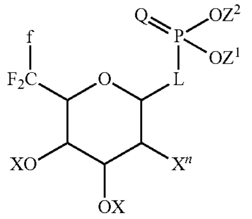

f is at the 6 position of the pyranose. It was found that having two or three F atoms at the 6 position allows the compounds according to the invention to successfully inhibit fucosylation, particularly through inhibition of 4,6-dehydratase activity. Two atoms at the 6 position are defined as F, and accordingly f can be F or H. As detailed later herein, the inhibitory mechanism for di-6-fluorides and tri-6-fluorides may not be identical, and therefore both options can allow for distinct technical effects. Accordingly, in some preferred embodiments f is H. In other preferred embodiments f is F. Most preferably f is F because excellent results were obtained with tri-6-fluorides.

X is a moiety that can form hydroxyl moieties for the hexose, or that can generally represent protecting groups for such hydroxyl moieties. Such protecting groups can later be converted into hydroxyl moieties, for instance after cellular uptake of the protected species. Accordingly, X is in each instance independently chosen from hydrogen and a linear, branched, or cyclic C1-4acyl or alkyl wherein each carbon atom is optionally substituted by a halogen, an alkoxy, or a haloalkoxy moiety, and wherein the acyl or alkyl is optionally unsaturated. For compounds with more direct activity, it is preferred that X is H. For compounds for which transport or conversion is desired prior to an inhibitory effect, it is preferred that X is a linear, branched, or cyclic C1-4acyl or alkyl wherein each carbon atom is optionally substituted by a halogen, an alkoxy, or a haloalkoxy moiety, and wherein the acyl or alkyl is optionally unsaturated. In preferred embodiments, X is in each instance independently chosen from hydrogen and a linear C1-4acyl wherein each carbon atom is optionally substituted by a halogen or a methoxy moiety. Most preferably X is H or acyl. Each instance of X can independently be selected as described above. In preferred embodiments, the same choice is made for each instance of X in a compound according to the invention. More features and definitions are provided below.

X″ is a moiety that resembles X in that it can form free or protected hydroxyl moieties, so that in preferred embodiments X″ is —O—X. However, being at the 2-position of the hexose, the inventors found that further moieties can be suitable here, particularly amines and protected forms thereof. Therefore, in other preferred embodiments, X″ is —$NH_2$, —NH—C1-4alkyl, —N(C1-4alkyl$_2$), —NH—C1-4acyl, or —N(C1-4acyl)$_2$ wherein each carbon atom is optionally substituted by a halogen, an alkoxy, or a haloalkoxy moiety, and wherein the acyl or alkyl is optionally unsaturated. In preferred embodiments, X″ is —O—X, —$NH_2$, or —NH—C1-4acyl, where a particularly preferred —NH—C1-4acyl is —NH-acetyl. More features and definitions are provided below.

L is at the 1 position of the hexose, and it connects the carbohydrate scaffold to the phosphoric moiety of the compound according to the invention. This phosphoric moiety can take several forms, and accordingly L can be O, S, NH, N($CH_3$), $CH_2$, CHF, or $CF_2$. When L is O, the phosphoric moiety is linked to the carbohydrate scaffold as a phosphoester, which is preferred for several embodiments where conventional metabolism of the compound of the invention is desired for some enzymes. The kinetics of such metabolism can be influenced by replacing this O by S, NH, or $N(CH_3)$, and therefore in other preferred embodiments L is O or S or NH or $N(CH_3)$, more preferably O or S or NH, even more preferably O or S. To disable some conversions of phosphoesters into further compounds, it can also be attractive when the compound is a phosphonate. This is the case when L is not a heteroatom, and therefore in preferred embodiments L is $CH_2$, CHF, or $CF_2$, of which $CF_2$ is preferred for its increased stability and electronic configuration. It is generally preferred that L is O, S, NH, or $CF_2$, more preferably O of $CF_2$, most preferably O. When L is O, S, NH, or $N(CH_3)$, it is preferred that Q is O. In preferred embodiments both L and Q are O.

Q is a substituent on phosphorous and can control the oxidation state of this phosphorous. When Q is O or S, the phosphorous is P(V) and can undergo further enzymatic conversion to for instance diphosphonucleosides. The behaviour of phosphorothioates as compared to analogues where Q is O is well known, and therefore in some preferred embodiments, Q is S. When Q is a lone pair, the compound is a phosphine, which can for instance be a useful synthetic intermediate. Most preferably Q is O.

$Z^1$ and $Z^2$ are moieties that can form either —OH moieties attached to the phosphorous atom, or that can form protected or further conjugated versions thereof. Accordingly, when unprotected compounds according to the invention are desired, preferably at least one of $Z^1$ and $Z^2$ is H, more preferably both are H. When a protected version of such a compound is required, at least one of $Z^1$ and $Z^2$ can be a protecting group, preferably both $Z^1$ and $Z^2$ can be protecting groups. $Z^1$ and $Z^2$ can together form a single protecting group. As a skilled person will understand, for salts of the compounds according to the invention, one or two of $Z^1$ and $Z^2$ can be absent, thus forming an anion.

Suitable protecting groups in this context are benzyl or a linear, branched, or cyclic C1-6 acyl, alkyl, alkenyl, or alkynyl, wherein each carbon atom is optionally substituted by a halogen, an alkoxy, or a haloalkoxy moiety; or a C1-4alkyl-Q'-C1-4acyl or a C1-4alkyl-Q'-C1-4alkyl, wherein each carbon atom is optionally substituted by a halogen, an alkoxy, or a haloalkoxy moiety, and wherein Q' is O or —O—C(═O)—O— or S or —S—S—; or $Z^1$ and $Z^2$ together form a C1-4alkyl bridging moiety that is optionally substituted with halogen or a C1-10hydrocarbon; or $Z^1$ is C5-6aryl and r forms an N-linked amino acid. In preferred embodiments Q' is O. In other preferred embodiments, Q' is S. Preferably, when multiple instances of O' are present, the same choice is made for each instance. Preferably, when at least one of $Z^1$ and $Z^2$ is a linear, branched, or cyclic C1-6 acyl, alkyl, alkenyl, or alkynyl moiety, it is a linear C1-4alkyl, wherein each carbon atom is optionally substituted by a halogen, an alkoxy, or a haloalkoxy moiety. Preferably, when at least one of $Z^1$ and $Z^2$ is a C1-4alkyl-Q'-C1-4acyl or a C1-4alkyl-Q'-C1-4alkyl, it is a C1-4alkyl-O—C1-4acyl, a C1-4alkyl-O—C1-4alkyl, a C1-4alkyl-S—C1-4acyl, or a C1-4alkyl-S—C1-4alkyl, wherein each carbon atom is optionally substituted by a halogen or a methoxy moiety. Preferably, when $Z^1$ and $Z^2$ together form a C1-4alkyl bridging moiety, $Z^1$ and $Z^2$ together form a C2-3alkyl bridging moiety. When $Z^1$ and $Z^2$ together form a C1-4alkyl bridging moiety that is substituted with a C1-10hydrocarbon, each carbon atom of said C1-10hydrocarbon is optionally substituted by further functional groups such as a halogen, an alkoxy, or a nitro moiety; preferably at most one carbon atom is optionally substituted by functional groups, of which a nitro moiety is most preferred. In preferred embodiments, $Z^1$ and $Z^2$ represent the same moiety. More features and definitions are provided below.

In preferred embodiments, $Z^1$ is H and $Z^2$ together with the O to which it is attached form a nucleotide. Examples are shown below.

(1-A)

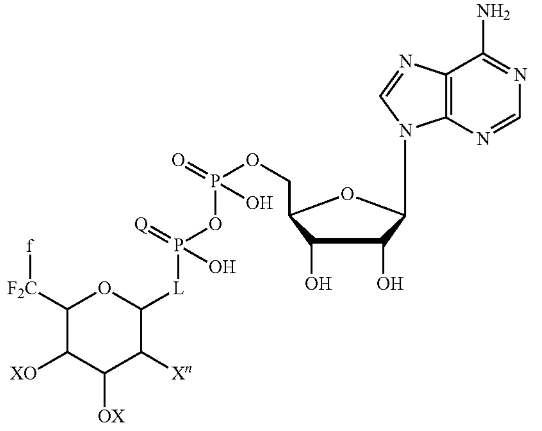

(1-C)

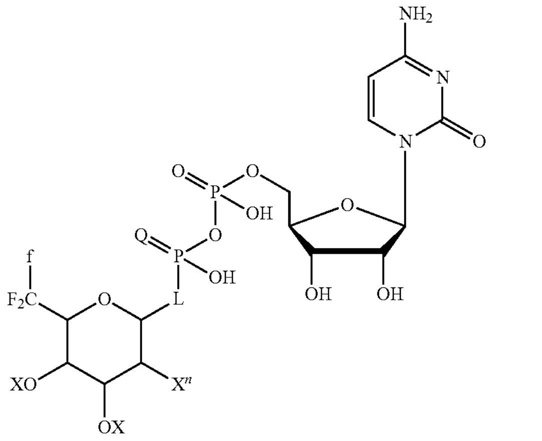

(1-G)

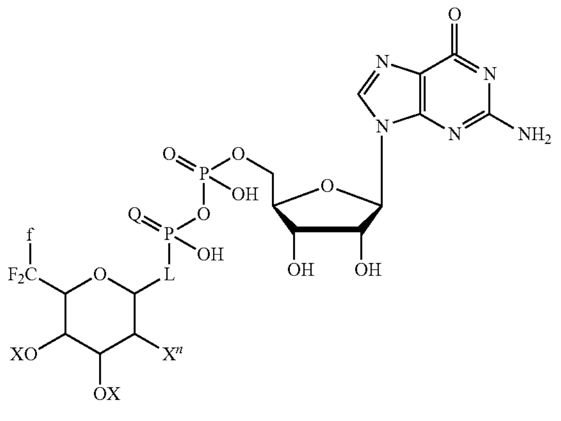

-continued (1-T)

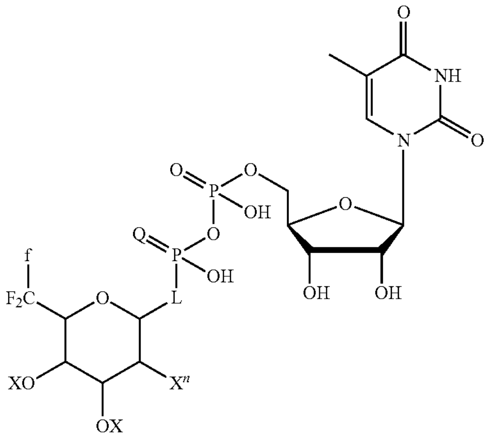

It should be noted that deoxyribosyl-analogues are also envisaged, and that a uracil base instead of a thymine base is also envisioned. Preferred embodiments wherein $Z^1$ is H and $Z^2$ together with the O to which it is attached form a nucleotide are of general formula (1-A), (1-C), (1-G), or (1-T), more preferably of generally formula (1-G). Herein, Q is preferably O. Herein, L is preferably O. More preferably both L and Q are O.

As used herein, C1-4alkyl refers to an alkyl having 1 to 4 carbon atoms. When not otherwise specified, it can be linear, branched, or cyclic, and it can be optionally unsaturated. In preferred embodiments such an alkyl is linear. In preferred embodiments such an alkyl is not unsaturated. A cyclic alkyl that is unsaturated can be an aromatic moiety. The same holds for alkyl with different numbers indicated, mutatis mutandis (C1-8 refers to an alkyl having 1 to 8 carbon atoms, etc.). Preferred alkyl groups are methyl, ethyl, propyl, propenyl, propargyl, butyl, butenyl, butynyl, cyclobutyl, pentyl, pentenyl, pentynyl, cyclopentyl, hexyl, cyclohexyl, phenyl, heptyl, and octyl. Preferred propyl groups are n-propyl, isopropyl, and cyclopropyl. Preferred butyl groups are n-butyl, 2-butyl, tert-butyl, and sec-butyl. Preferred pentyl groups are n-pentyl, 2-pentyl, 3-pentyl, 3-methyl-n-butyl, 2,2-dimethyl-n-propyl, 1,1-dimetyl-n-propyl, and cyclopentyl. Preferred hexyl groups are n-hexyl, cyclohexyl, and phenyl.

As used herein, C1-4acyl refers to an acyl having 1 to 4 carbon atoms. When not otherwise specified, it can be linear, branched, or cyclic, and it can be optionally unsaturated. In preferred embodiments such an acyl is linear. In preferred embodiments such an acyl is not unsaturated. A cyclic acyl that is unsaturated can comprise an aromatic moiety such as forming a benzoyl moiety. The same holds for acyl with different numbers indicated, mutatis mutandis (C1-8 refers to an acyl having 1 to 8 carbon atoms, etc.). Preferred acyl groups are $C(O)CH_3$, $C(O)CH_2CH_3$, C(O)phenyl, and C(O) $CH_2$-phenyl.

Acyl or alkyl can be optionally substituted by a halogen, an alkoxy, or a haloalkoxy. A halogen is preferably F, C1, Br, or I, more preferably F or C1, most preferably F. An alkoxy is preferably of general formula —O—C1-8alkyl, more preferably —O—C1-4alkyl, most preferably it is methoxy. Haloalkoxy is preferably as described for alkoxy, featuring one, two or three halogen substitutions as described for halogen. In preferred embodiments, all hydrogen atoms of the haloalkoxy moiety are substituted by halogen, preferably by F. A preferred haloalkoxy is $CF_3$.

A hydrocarbon as used herein has the amount of carbon atoms as indicated, and can be an alkyl or acyl moiety as described herein. It can be saturated or unsaturated, and optionally substituted as described above. A preferred hydrocarbon is a phenyl moiety.

Preferred examples for X are in each instance independently chosen from acetyl, propionyl, and butyryl, preferably it is acetyl. Preferred examples for $X^1$ are —OX and —$NH_2$ and —NH-acetyl.

Preferred examples for $Z^1$ and $Z^2$ are methyl, ethyl, acetyl, acyloxy alkyl as shown below, alkoxy carbonyl oxy alkyl as shown below, S-acylthioalkyl ester (SATE) as shown below, dithiol-thioethanol as shown below, together forming an optionally substituted C3alkyl bridging moiety as shown below, optionally substituted cyclosal bridging moiety as shown below, nitro cyclosal bridging moiety as shown below, and the compounds of general formula (1-A), (1-C), (1-G), or (1-T).

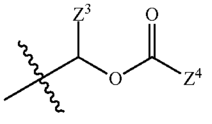

acyloxy alkyl

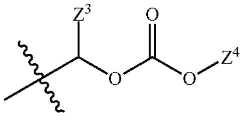

alkoxy carbonyl oxy alkyl

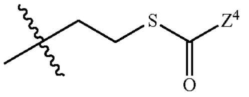

S-acylthioalkyl ester

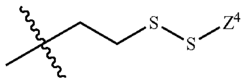

dithiol-thioethanol

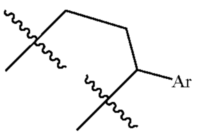

optionally substituted C3alkyl bridging moiety

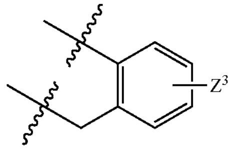

optionally substituted cyclosal bridging moiety

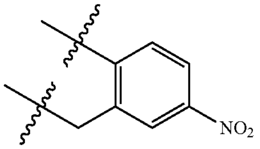

Nitro cyclosal bridging moiety

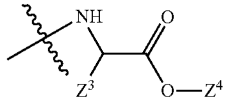

N-linked amino acid derivative

When $Z^x$ is not $OZ^2$, it is an N-linked amino acid derivative as shown above. $Z^3$ can be H or optionally substituted C1-7alkyl, it is preferably H or methyl or ethyl or an amino acid side chain, more preferably H or methyl, most preferably H. Amino acid side chains are known in the art. Examples are —H, —$CH_3$, —$CH_2$-phenyl, —$CH_2$-(4-hydroxyphenyl), —$CH_2$—OH, —$C(CH_3)(CH_2$—OH), et cetera. When $Z^3$ is an amino acid side chain, preferably $Z^4$ is 2-isopropyl. $Z^4$ can be H or optionally substituted C1-7alkyl, it is preferably methyl or ethyl or benzyl, more preferably methyl or ethyl, most preferably ethyl.

When $Z^x$ is an N-linked amino acid derivative, it is preferred that $Z^1$ is H or C5-6aryl, more preferably C5-6aryl such as phenyl. When an optionally substituted C3alkyl bridging moiety is formed, Ar can be H or C5-6aryl, preferably it is C5-6aryl, more preferably it is phenyl.

The stereochemistry of the compounds according to the invention can be relevant for influencing their selectivity as substrates for specific 4,6-dehydratases. Accordingly, in preferred embodiments is provided the compound according to the invention, wherein it is of general formula (1-man), (1-gluc), (1-fuc), or (1-gal):

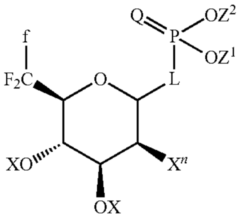
(1-man)

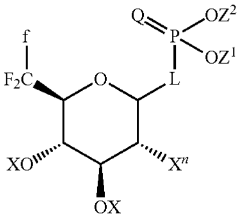
(1-gluc)

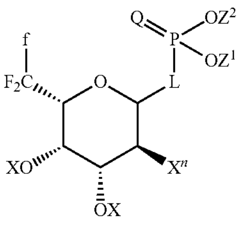
(1-fuc)

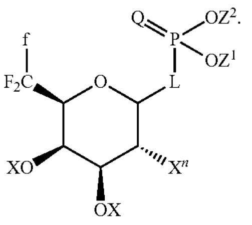
(1-gal)

In the above general formulas $OZ^2$ can also be $Z^x$. In some embodiments, the compounds are of general formula (1-man), (1-gluc), or (1-fuc). In some embodiments, the compounds are of general formula (1-man), (1-gluc), or (1-gal). In some embodiments, the compounds are of general formula (1-man), (1-gal), or (1-fuc). In some embodiments, the compounds are of general formula (1-gal), (1-gluc), or (1-fuc). In some embodiments, the compounds are of general formula (1-man) or (1-gluc). In some embodiments, the compounds are of general formula (1-man) or (1-fuc). In some embodiments, the compounds are of general formula (1-man) or (1-gal). In some embodiments, the compounds are of general formula (1-fuc) or (1-gluc). In some embodiments, the compounds are of general formula (1-gal) or (1-gluc). In some embodiments, the compounds are of general formula (1-fuc) or (1-gal). In preferred embodiments, the compounds are of general formula (1-fuc). In preferred embodiments, the compounds are of general formula (1-man). In preferred embodiments, the compounds are of general formula (1-gluc). In preferred embodiments, the compounds are of general formula (1-gal). Even more preferred are compounds of general formula (1-man) or (1-gluc), preferably wherein f is F. Most preferably these compounds are of general formula (1-man). A compound of general formula (1-man) can have D or L stereochemistry, preferably it is D. A compound of general formula (1-gluc) can have D or L stereochemistry, preferably it is D. A compound of general formula (1-fuc) can have D or L stereochemistry, preferably it is L. A compound of general formula (1-gal) can have D or L stereochemistry, preferably it is D.

In preferred embodiments is provided the compound according to the invention, wherein $Z^x$ is $OZ^2$, and f is F; and/or X is in each instance independently chosen from hydrogen and a linear C1-4acyl wherein each carbon atom is optionally substituted by a halogen or a methoxy moiety; and/or X″ is —O—X, —$NH_2$, or —NH—C1-4acyl; and/or L is O, S, NH, or $CF_2$; and/or Q is O; and/or $Z^1$ and $Z^2$ are each independently chosen from hydrogen, a linear C1-4alkyl, wherein each carbon atom is optionally substituted by a halogen, an alkoxy, or a haloalkoxy moiety, a C1-4alkyl-O—C1-4acyl, a C1-4alkyl-O—C1-4alkyl, a C1-4alkyl-S—C1-4acyl, or a C1-4alkyl-S—C1-4alkyl, wherein each carbon atom is optionally substituted by a halogen or a methoxy moiety, or $Z^1$ and $Z^2$ together form an optionally substituted C2-3alkyl bridging moiety, or $Z^1$ is H and $Z^2$ together with the O to which it is attached form a nucleotide.

More preferably,

X is in each instance chosen from acetyl, propionyl, and butyryl, preferably it is acetyl; and/or $Z^1$ is chosen from hydrogen, —$CH_2CH_2$—S-acetyl, and —$CH_2CH_2$—O-acetyl; and/or $Z^2$ is chosen from hydrogen, —$CH_2CH_2$—S-acetyl, and —$CH_2CH_2$—O-acetyl;

or $Z^1$ and $Z^2$ together form —$CH_2$—$CH_2$— or —$CH_2$—$CH_2$—$CH_2$— or —$CH_2$—$CH_2$—CH(C5-6aryl)-.

Preferred compounds according to the invention are of general formula (1) and have:

f=H, each X is H, X″ is OH, L is O, Q is O, $Z^1$ and $Z^2$ are —$CH_2CH_2$—S-acetyl;

f=F, each X is H, X″ is OH, L is O, Q is O, $Z^1$ and $Z^2$ are —$CH_2CH_2$—S-acetyl;

f=H, each X is acetyl, X″ is O-acetyl, L is O, Q is O, $Z^1$ and $Z^2$ are —$CH_2CH_2$—S-acetyl;

f=F, each X is acetyl, X″ is O-acetyl, L is O, Q is O, $Z^1$ and $Z^2$ are —$CH_2CH_2$—S-acetyl;

f=H, each X is H, X″ is OH, L is O, Q is O, $Z^1$ and $Z^2$ are H;

f=F, each X is H, X″ is OH, L is O, Q is O, $Z^1$ and $Z^2$ are H;

f=H, each X is acetyl, X″ is O-acetyl, L is O, Q is O, $Z^1$ and $Z^2$ are H;

f=F, each X is acetyl, X″ is O-acetyl, L is O, Q is O, $Z^1$ and $Z^2$ are H;

wherein more preferably the compounds are of general formula 1-man.

In preferred embodiments, the compound according to the invention is not of general formula (1) wherein (A) the compound is of general formula (1-man) wherein f is H, each X is H, X″ is —OH, L is O, Q is O, $Z^x$ is $OZ^2$, and $Z^1$ and $Z^2$ are H;

(B) the compound is of general formula (1-gluc) wherein f is H, optionally the compound of general formula (1-gluc) wherein f is H, each X is H, X″ is —OH, L is O, Q is O, $Z^x$ is $OZ^2$, and $Z^1$ and $Z^2$ are H or benzyl, preferably H, or wherein f is H, each X is acetyl, X″ is —O-acetyl, L is O, Q is O, $Z^x$ is $OZ^2$, and $Z^1$ and $Z^2$ are benzyl;

(C) the compound is of general formula (1-fuc) wherein f is F (D) the compound is of general formula (1-gal) wherein f is H, each X is H, X″ is —OH, L is O, Q is O, $Z^x$ is $OZ^2$, and $Z^1$ and $Z^2$ are H.

In preferred embodiments the compound is not as described above under (A). In preferred embodiments the compound is not as described above under (B). In preferred embodiments the compound is not as described above under (C). In preferred embodiments the compound is not as described above under (D). In preferred embodiments the compound is not as described above under (A) or (B). In preferred embodiments the compound is not as described above under (A) or (C). In preferred embodiments the compound is not as described above under (A) or (D). In preferred embodiments the compound is not as described above under (B) or (C). In preferred embodiments the compound is not as described above under (B) or (D). In preferred embodiments the compound is not as described above under (C) or (D). In preferred embodiments the compound is not as described above under (A) or (B) or (C). In preferred embodiments the compound is not as described above under (A) or (B) or (D). In preferred embodiments the compound is not as described above under (A) or (C) or (D). In preferred embodiments the compound is not as described above under (B) or (C) or (D). In preferred embodiments the compound is not as described above under (A) or (B) or (C) or (D).

Compositions

In another aspect, the invention provides a composition comprising a compound according to the invention and a pharmaceutically acceptable excipient. Such a composition is referred to herein as a composition according to the invention. Preferably, such a composition is formulated as a pharmaceutical composition. A preferred excipient is water, preferably purified water, more preferably ultrapure water. Further preferred excipients are adjuvants, binders, desiccants, or diluents. Further preferred compositions additionally comprise additional medicaments for treating cancer or for treating conditions as described later herein. Preferred additional medicaments in this regards are chemotherapeutic agents, immunotherapeutic agents, or steroids for the treatment of cancer, or antiviral agents, or antibacterial agents.

Preferably, a composition according to the invention further comprises a delivery vehicle. In said delivery vehicle, a compound according to the invention is contained in the delivery vehicle or is attached to the delivery vehicle. Accordingly, a compound according to the invention may be present in or attached to the delivery vehicle. A preferred delivery vehicle in a composition according to the present invention is a nanoparticle or an antibody or an antibody conjugate. In case the delivery vehicle is an antibody or an antibody conjugate, the compound according to the invention is attached to the delivery vehicle; the antibody is preferably an anti-tyrosinase related protein-1 antibody. A nanoparticle according to the present invention is preferably a poly(lactic-co-glycolic acid) (PLGA) based nanoparticle. Preferably, a nanoparticle according to the present invention comprises a targeting device. Such a targeting device may be any compound that is capable of targeting the delivery vehicle, in vitro, ex vivo or in vivo, to a predetermined target. The predetermined target may be a microbiological cell or a tumor cell, preferably a tumor cell, more preferably a melanoma cell. A preferred targeting device according to the present invention is an antibody which may be polyclonal but preferably is monoclonal. A preferred antibody is an anti-tyrosinase related protein-1 antibody to target the nanoparticle according to the invention to a melanoma cell. Further preferred delivery vehicles are liposomes, polymersomes, and protein cages.

4,6-Dehydratases

Central to the invention was the realisation by the inventors that a cell-active fucosylation inhibitor could be designed by 6-deoxy-di- or tri-fluoride modification of a substrate, optionally using esters protecting the e.g. mannose-1-phosphate. The esters at X, $X^1$, $Z^1$ and $Z^2$ can help make the inhibitor cell membrane permeable and allow the molecule to enter the natural metabolism towards the GDP-mannose analog after which it acts on the de novo biosynthesis of GDP-fucose. Interestingly, both di- and tri-fluorides were active. The activity is in inhibition of hexose-4,6-dehydratases. FIG. 2 represents a mechanism for 4,6-dehydratase inhibition. Examples of known hexose-4,6-dehydratases are rfbG (CDP-glucose 4,6-dehydratase [EC:4.2.1.45]), rfbB (or rmlB, or rffG; dTDP-glucose 4,6-dehydratase [EC:4.2.1.46]), gmd (or GMDS; GDP-mannose 4,6-dehydratase [EC:4.2.1.47]), RHM (or UDP-glucose 4,6-dehydratase [EC:4.2.1.76]), pseB (or UDP-N-acetylglucosamine 4,6-dehydratase [EC:4.2.1.115]), pglF (or UDP-N-acetyl-D-glucosamine 4,6-dehydratase [EC:4.2.1.135]), ncsC1 (or NDP-hexose 4,6-dehydratase). In the context of this invention, a particularly preferred 4,6-dehydratase is GMDS.

In the context of this invention, the term hexoses should not be so narrowly construed as to only encompass literal hexa-hydrates. Variants are also to be encompassed. Herein, variants such as for instance deoxy-hexoses and hexosamines are also referred to when reference is broadly made to hexoses. Importantly, hexose-4,6-dehydratases thus also encompass for instance deoxyhexose-4,6-dehydratases and hexosamine-4,6-dehydratases.

Not all compounds according to the invention are inhibitors of 4,6-dehydratases. Some compounds are precursors for such inhibitors, or prodrugs. For instance, when $X''$ is $NH_2$ the compound can be intracellularly metabolized towards an analogue where $X''$ is N-acetyl. When an X is not H, the compound can be intracellularly metabolized towards an analogue where X is H. Such conversions have been described in the art for other carbohydrate-based compounds, and a skilled person is aware of these options.

An inhibitor can achieve inhibitory activity when used at an effective concentration. An inhibitory activity is preferably an activity that reduces the activity of its target enzyme by at least 10%, more preferably by at least 50%, even more preferably by at least 90%, most preferably by at least 99%. Preferably, the $EC_{50}$ of an inhibitor is at most 1 mM, more preferably at most 500 micromolar, even more preferably at most 400, 300, 250, 200, 150, or 100 micromolar, even more preferably at most 50 micromolar, or 45, 40, 35, 30, 25, 20, or 15 micromolar, most preferably at most 10 micromolar or at most 5, 4, 3, 2, or 1 micromolar. Inhibitory activity and associated values can be determined using methods known in the art, for instance such as described in the examples.

In preferred embodiments, inhibitory activity is still at about 25% of its maximal activity three 10 days after application or administration of the inhibitor. More preferably it is still at 30%, 40%, 50%, or 60% after three days. Most preferably it is at least at 50% of its original activity after three days. Such persistence of activity is preferably assessed using lectin binding, more preferably using the AAL or AOL lectin.

Use of the Compounds

In one aspect, the invention provides a method for inhibiting a hexose-4,6-dehydratase, the method comprising the step of contacting the hexose-4,6-dehydratase with a compound according to the invention, or with a composition according to the invention. Preferably, the hexose-4,6-dehydratase is CDP-glucose 4,6-dehydratase, dTDP-glucose 4,6-dehydratase, GDP-mannose 4,6-dehydratase, UDP-glucose 4,6-dehydratase, UDP-N-acetylglucosamine 4,6-dehydratase (also known as configuration retaining UDP-N-acetylglucosamine 4,6-dehydratase), or UDP-N-acetyl-D-glucosamine 4,6-dehydratase (also known as configuration inverting UDP-N-acetylglucosamine 4,6-dehydratase). This method is referred to herein as a method according to the invention, and it can be an in vitro, in vivo, or ex vivo method. Preferably it is an in vitro method.

In preferred embodiments, the invention provides the method according to the invention, wherein the hexose-4, 6-dehydratase is in a cell, and the method further comprises the steps of:

i) contacting the cell with a compound according to the invention, with a compound for use according to the invention, or with a composition according to the invention; and ii) allowing the compound to passively diffuse into the cell, and/or to be actively taken up by the cell; preferably, allowing the compound to passively diffuse into the cell;

wherein for the compound according to the invention or for the compound for use according to the invention preferably X is not H, and/or preferably X" is not $NH_2$, and/or preferably $Z^1$ and $Z^2$ are not H.

When each of X and $Z^1$ and $Z^2$ are hydrogen and/or when X" is $NH_2$, preferably in step ii) the compound is allowed to be actively taken up by the cell, which is preferably a bacterial cell. When none of X and $Z^1$ and $Z^2$ are hydrogen and/or X" is not $NH_2$, or when only one or both of $Z^1$ and $Z^2$ are hydrogen, preferably in step ii) the compound is allowed to passively diffuse into the cell. This method is preferably for reducing fucosylation of the cell. When X" is $NH_2$ the compound according to the invention can be actively taken up by a cell, after which the compound can be metabolized towards an N-acetyl compound that can be a substrate for the 4,6-dehydratase.

The cell in which fucosylation is reduced, or in which the 4,6-dehydratase is present, is preferably a cancer cell, a bacterial cell, or a cell at risk of being infected by a virus; more preferably it is a cancer cell or a bacterial cell. Reduction of fucosylation can promote recognition of a bacterial cell or of a cancer cell by immune cells, or it can prevent infection of a host cell by a virus. Reduction of fucosylation can decrease extravasation of cells via selectin receptor binding.

Reduction of fucosylation can also advantageously be used to produce afucosyloglycoproteins. Whenfucosyl residues are not incorporated in glycoproteins, the resulting proteins are known as afucosyloglycoproteins. The exposure of the subterminal residues can result in rapid clearance of the afucosyloglycoproteins from the circulation, for example through afucosyloglycoprotein receptors on specialized white blood cells such as macrophages, more particularly Kupffer cells. This can lead to attenuation of autoimmune disease (Pagan et al., 2018, doi: 10.1016/j.cell.2017.11.041). Accordingly, preferred methods of the invention are for the production of afucosyloglycoprotein.

In this context, prevention of incorporation of fucose in the glycocalyx can be an attractive purpose for a method. When L is not O, more preferably when L is $CH_2$, CHF, or $CF_2$, the compounds according to the invention can be used in a method for prevention incorporation of fucose or fucose analogues in the glycocalyx of a cell.

Medical Use of the Compounds

In another aspect, the invention provides the compound according to the invention for use as a medicament. Particularly, the invention provides a compound of general formula (1) as shown earlier herein with definitions as provided earlier herein or a salt thereof, or of general formula (Iz) as shown below or a salt thereof:

(1z)

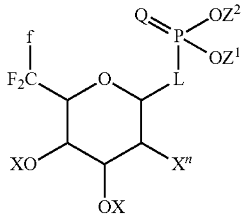

wherein f is H or F;

X is in each instance independently chosen from hydrogen and a linear, branched, or cyclic C1-4acyl or alkyl wherein each carbon atom is optionally substituted by a halogen, an alkoxy, or a haloalkoxy moiety, and wherein the acyl or alkyl is optionally unsaturated; X" is —O—X, —$NH_2$, —NH—C1-4alkyl, —N(C1-4alkyl$_2$), —NH—C1-4acyl, or —N(C1-4acyl)$_2$ wherein each carbon atom is optionally substituted by a halogen, an alkoxy, or a haloalkoxy moiety, and wherein the acyl or alkyl is optionally unsaturated;

L is O, S, NH, N($CH_3$), $CH_2$, CHF, or $CF_2$;

Q is O or S;

$Z^1$ and $Z^2$ are each independently chosen from hydrogen, benzyl or a linear, branched, or cyclic C1-6 acyl, alkyl, alkenyl, or alkynyl, wherein each carbon atom is optionally substituted by a halogen, an alkoxy, or a haloalkoxy moiety, a C1-4alkyl-Q'-C1-4acyl or a C1-4alkyl-Q'-C1-4alkyl, wherein each carbon atom is optionally substituted by a halogen, an alkoxy, or a haloalkoxy moiety, and wherein Q' is O or —O—C(═O)—O— or S or —S—S—, or $Z^1$ and $Z^2$ together form a C1-4alkyl bridging moiety that is optionally substituted with halogen or a C1-10hydrocarbon, or $Z^1$ is H and $Z^2$ together with the O to which it is attached form a nucleotide, for use as a medicament, wherein the medicament is preferably for use in the treatment of cancer, tumor metastasis, inflammation, infections, or genetic disorders. Such a compound is referred to herein as a compound for use according to the invention. Additionally, the invention provides the composition according to the invention, for use as a medicament, wherein the medicament is preferably for use in the treatment of cancer, tumor metastasis, inflammation, infections, or genetic disorders. Such a composition is referred to herein as a composition for use according to the invention.

In preferred embodiments, the medicament is for use in treating, preventing, or delaying cancer, tumor metastasis, inflammation, infections, or genetic disorders. In more preferred embodiments, the medicament is for use in treating, preventing, or delaying cancer, tumor metastasis, inflammation, infections, more preferably cancer. A compound for use according to the invention can conveniently be combined with state of the art cancer therapies such as, but not limited to cancer medicaments, radiation, surgical procedures, chemotherapy, immunotherapy, targeted therapies or a combination thereof. Similarly, it can be combined with the administration of antiviral or antibacterial agents.

In particular embodiments, the invention provides the use of a compound according to the invention or of a composition according to the invention for the manufacture of a medicament, preferably a medicament for the treatment, prevention, or delay of cancer, tumor metastasis, inflammation, infections, more preferably cancer.

Formulation of medicaments, ways of administration, and the use of pharmaceutically acceptable excipients are known and customary in the art and for instance described in Remington; The Science and Practice of Pharmacy, 21st Edition 2005, University of Sciences in Philadelphia.

The medical use and methods according to this aspect of the present invention can be used to treat various subjects. A preferred subject is a subject in need of treatment, which can be a subject suffering from a disease or condition, or a subject expected to develop, or at risk of developing, a disease or condition. A preferred subject is a human or an animal subject. In preferred embodiments, a subject is not human.

In the context of this invention, a preferred cancer is neuroblastoma, glioma, leukaemia, lung cancer, bladder cancer, renal cancer, pancreatic cancer, adenocarcinoma, or epithelial cancer, and more preferably melanoma. Preferred examples of epithelial cancer are colorectal cancer, breast cancer, head and neck cancer, and prostate cancer. The treatment, prevention or delay of cancer is preferably the treatment, prevention or delay of cancer metastasis.

The medical use as described herein is suitable for implementing a method of treating, preventing, or delaying cancer, tumor metastasis, inflammation, infections, or genetic disorders in a subject in need thereof, the method comprising the step of administering to the subject an effective amount of a compound according to the invention, or a composition according to the invention.

Administration may be performed through any suitable route including but not limited to: oral, aerosol or other device for delivery to the lungs, nasal spray, intravenous, intramuscular, subcutaneous, intradermal, intraperitoneal, intrathecal, vaginal, rectal, topical, lumbar puncture, intrathecal, intratumoral, peritumoral. A combination, a composition, compositions or a single composition according to the present invention may be administered to a subject or to a cell, tissue, tumor or organ of said subject for at least one week, one month, six month, one year or more. The frequency of administration of combination, a composition, compositions or a single composition according to the present invention may depend on several parameters such as the medical condition of the patient. The frequency may be ranged between at least once, two, three, four times a day, a week, or two weeks, or three weeks or four weeks or five weeks or a longer time period. The use may be combined with the use of an immune adjuvant, preferably at a dose that is ranged from 0.1 to 30 mg/kg body weight, preferably from 0.5 to 20 mg/kg, more preferably from 1 to 10 mg/kg, more preferably from 2 to 5 mg/kg of the immune adjuvant, more preferably 3 mg/kg. Preferred adjuvants are described above.

The dosage of the compound for use according to the invention is preferably ranged from 1 to 50 mg/kg body weight, preferably from 5 to 20 mg/kg, more preferably from 5 to 15 mg/kg, more preferably from 7 to 12 mg/kg of the immune adjuvant, more preferably 10 mg/kg.

General Definitions

Throughout this application, the term "fucosylation inhibitor" is generally interchangeable with the term "fucose biosynthesis inhibitor". In preferred embodiments, compounds and compositions according to the invention are for use in methods according to the invention, or are for use according to the invention. Each embodiment as identified herein may be combined together unless otherwise indicated.

When a structural formula or chemical name is understood by the skilled person to have chiral centers, yet no chirality is indicated, for each chiral center individual reference is made to all three of either the racemic mixture (having any enantiomeric excess), the pure R enantiomer, and the pure S enantiomer. Whenever a fragment of a molecule, often referred to as a moiety, is represented, a dotted or wavy line indicates which bond links it to the entirety of the molecule; alternately, an asterisk (*) indicates where the represented moiety is linked to the rest of the molecule. This asterisk does not imply an atom, and neither does a bond that is crossed by a dotted or wavy line convey information about which atom is at the non-moiety side of the bond. All this is known in the art, and is routine practice.

Compounds and compounds for use provided in this invention can be optionally substituted. Suitable optional substitutions are replacement of —H by a halogen. Preferred halogens are F, Cl, Br, and I. Further suitable optional substitutions are substitution of one or more —H by $—NH_2$, —OH, =O, alkyl, alkoxy, haloalkyl, haloalkoxy, alkene, haloalkene, alkyne, haloalkyn, and cycloalkyl. Alkyl groups have the general formula $C_nH_{2n+1}$ and may alternately be linear or branched. Unsubstituted alkyl groups may also contain a cyclic moiety, and thus have the concomitant general formula $C_nH_{2n-1}$. Optionally, the alkyl groups are substituted by one or more substituents further specified in this document. Examples of alkyl groups include methyl, ethyl, propyl, 2-propyl, t-butyl, 1-hexyl, 1-dodecyl, etc. Throughout this application, the valency of atoms should always be fulfilled, and H can be added or removed as required.

Unless stated otherwise, —H may optionally be replaced by one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_8$-$C_{12}$ cycloalkynyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo and silyl groups, wherein the silyl groups can be represented by the formula $(R^2)_3Si—$, wherein $R^2$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more heteroatoms selected from the group consisting of O, N and S. Preferably, these optional substitutions comprise no more than twenty atoms, more preferably no more than fifteen atoms.

Whenever a parameter of a substance is discussed in the context of this invention, it is assumed that unless otherwise specified, the parameter is determined, measured, or manifested under physiological conditions. Physiological conditions are known to a person skilled in the art, and comprise aqueous solvent systems, atmospheric pressure, pH-values between 6 and 8, a temperature ranging from room temperature to about 37° C. (from about 20° C. to about 40° C.), and a suitable concentration of buffer salts or other components. It is understood that charge is often associated with equilibrium. A moiety that is said to carry or bear a charge is a moiety that will be found in a state where it bears or carries such a charge more often than that it does not bear or carry such a charge. As such, an atom that is indicated in this disclosure to be charged could be non-charged under specific conditions, and a neutral moiety could be charged under specific conditions, as is understood by a person skilled in the art.

In the context of this invention, a decrease or increase of a parameter to be assessed means a change of at least 5% of the value corresponding to that parameter. More preferably, a decrease or increase of the value means a change of at least 10%, even more preferably at least 20%, at least 30%, at least 40%, at least 50%, at least 70%, at least 90%, or 100%. In this latter case, it can be the case that there is no longer a detectable value associated with the parameter.

The use of a compound or composition as a medicament as described in this document can also be interpreted as the use of said compound or composition in the manufacture of a medicament. Similarly, whenever a compound or composition is used for as a medicament, it can also be used for the manufacture of a medicament, or in a method.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 1% of the value.

All patent and literature references cited in the present specification are hereby incorporated by reference in their entirety.

In the context of this invention, a cell or a sample can be a cell or a sample from a sample obtained from a subject. Such an obtained sample can be a sample that has been previously obtained from a subject. Such a sample can be obtained from a human subject. Such a sample can be obtained from a non-human subject.

A salt is preferably a pharmaceutically acceptable salt. A salt is preferably a base addition salt wherein at least one of $Z^1$ or $Z^2$ is absent and a cationic counterion is present. In other words $Z^1$ and $Z^2$ could be said to represent such a counterion, preferably cationic, wherein the O to which $Z^1$ or $Z^2$ is attached is negatively charged. Examples of suitable salts are non-metallic salts such as ammonia salts, and metallic salts such as sodium salts and potassium salts. A skilled person can select suitable salt forms, and their means of production are well known (see e.g. "Occurrence of pharmaceutically acceptable anions and cations in the Cambridge Structural Database" Haynes et al., DOI: 10.1002/jps.20441). A salt can also be an acid addition salt, for instance when $X''$ comprises nitrogen. Acid addition salts are known in the art and examples are HCl salts and acetic acid salts. When $Z^2$ is defined for an embodiment, r is preferably $OZ^2$. Herein, boldface can be used in variables to assist the reader; it does not imply further definition.

EXAMPLES

Example 1—Synthesis

General Procedures $^1H$ and $^{13}C$ NMR spectra were recorded on a Varian Inova 400 MHz or Bruker Avance III 500 MHz spectrometer. Chemical shifts are reported in parts per million (ppm)

relative to tetramethylsilane (TMS) as the internal standard. NMR data is presented as follows: Chemical shift, multiplicity (s=singlet, bs=broad singlet, d=doublet, t=triplet, dd=doublet of doublet, dt=doublet of triplet, m=multiplet and/or multiple resonances), integration, coupling constant in Hertz (Hz). All NMR signals were assigned on the basis of $^{1}H$, $^{13}C$, $^{19}F$ NMR, COSY and HSQC experiments. Mass spectra were recorded on a JEOL JMS-T100CS AccuTOF mass spectrometer. Automatic column chromatography was performed on Biotage Isolera Spektra One, using SNAP cartridges 10-50 g filled with normal silica (Biotage, 30-100 μm, 60 Å) or water resistant iatro beads. Microwave reactions were perfOCH3d on a Biotage Initiator 4.1.3. TLC analysis was conducted on TLC Silicagel, 60, F254, Merck, with detection by UV absorption (254 nm) where applicable, and by spraying with 20% sulfuric acid in methanol followed by charring at −150° C. or by spraying with a solution of $(NH\text{-}4)_6Mo_7O_{24}\cdot H_2O$ (25 g I-1) in 10% sulfuric acid in methanol followed by charring at ~300° C. DCM, ACN and Tol were freshly distilled. All reactions were carried out under an argon atmosphere. All synthesized samples that were used for cell tests were dissolved in water or a mixture of dioxane/water and subsequently lyophilized.

Commonly Used Abbreviations

Figure 1:
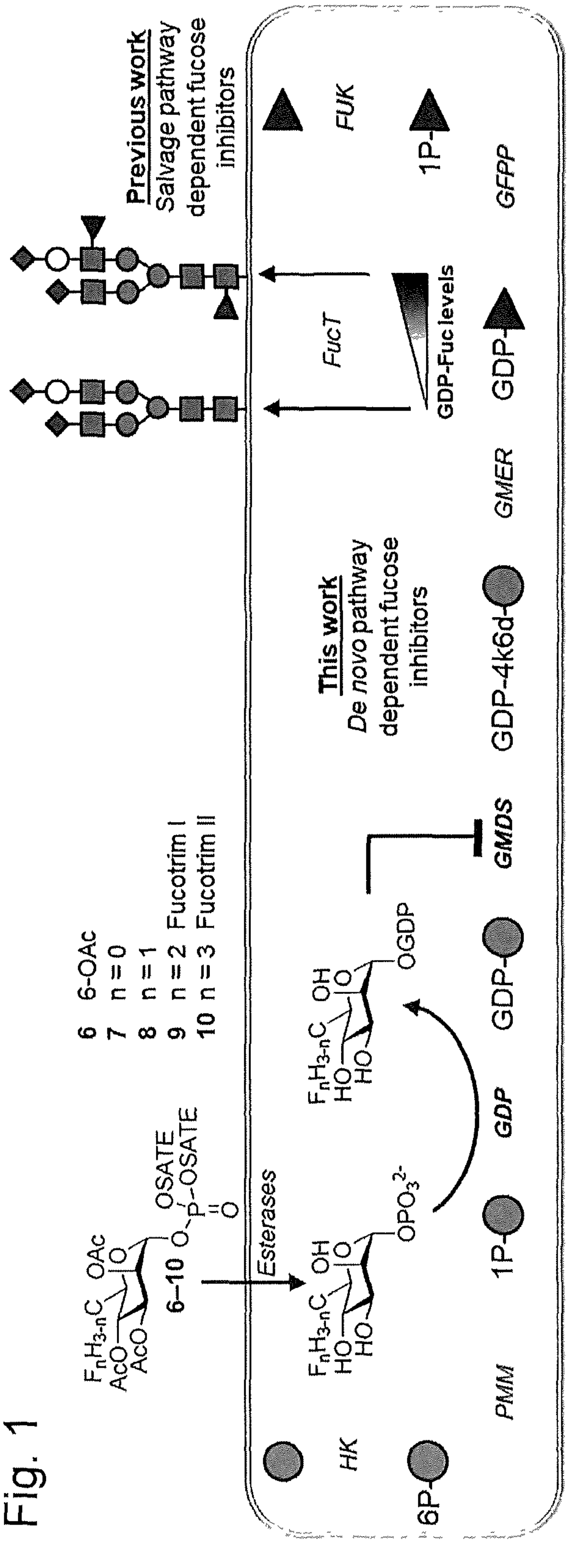
FIG. 1: Working model of metabolic fucosylation inhibitors.
Figure 2:
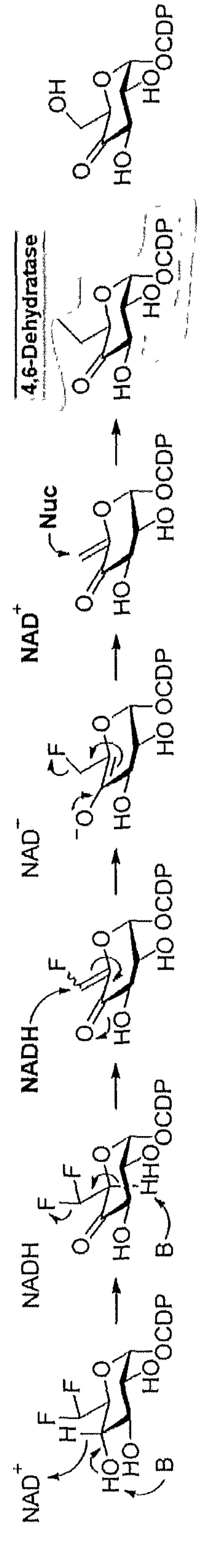
FIG. 2: Mechanism of action of 4,6-dehydratase inhibitors.
Figure 3A:
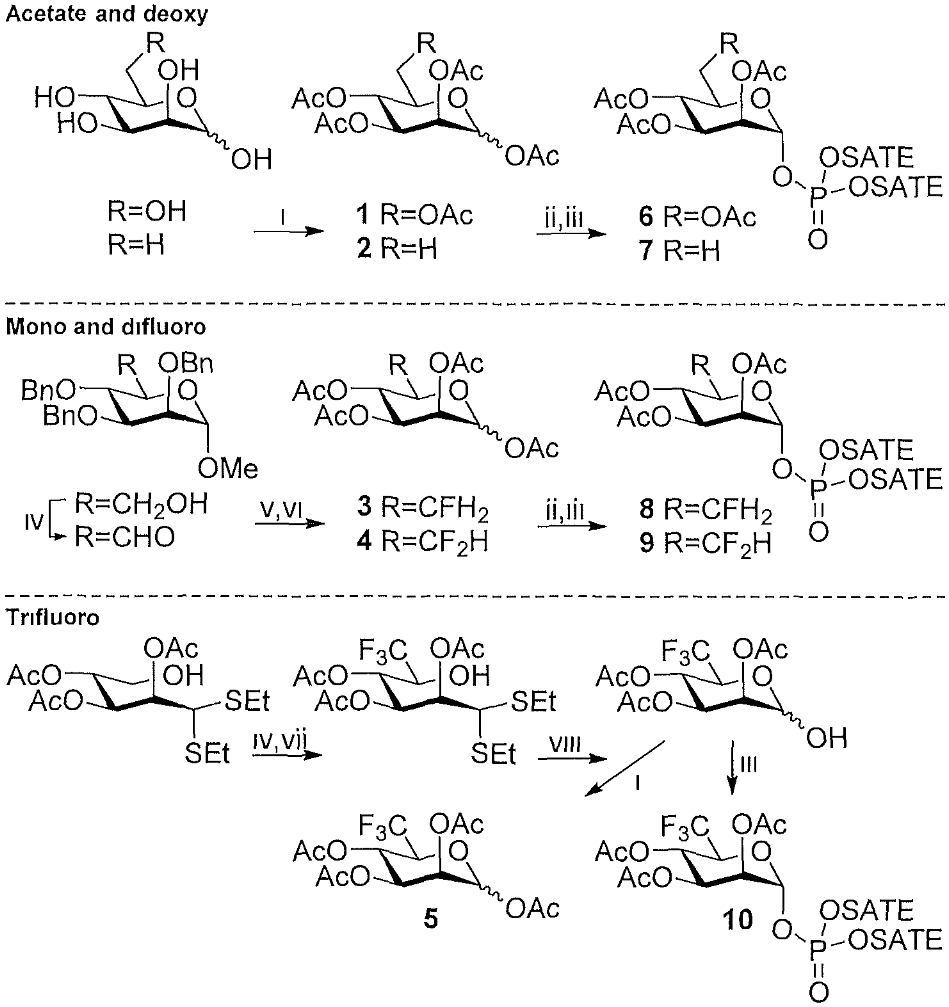
FIG. 3A: Synthesis of 1-10. i) $Ac_2O$, Pyr; ii) $H_2NNH_2 \cdot HOAc$, DMF; iii) bis(S-acetyl-2-thioethyl)N,N-diethylphosphoramidite, 1H-tetrazole, ACN, then mCPBA; iv) DMP, $NaHCO_3$, DCM; v) DAST, DCM; vi) $Ac_2O$, $H_2SO_4$, AcOH; vii) $TMSCF_3$, TBAF, THF; viii) NBS, $H_2O$/acetone.
Figure 3B:
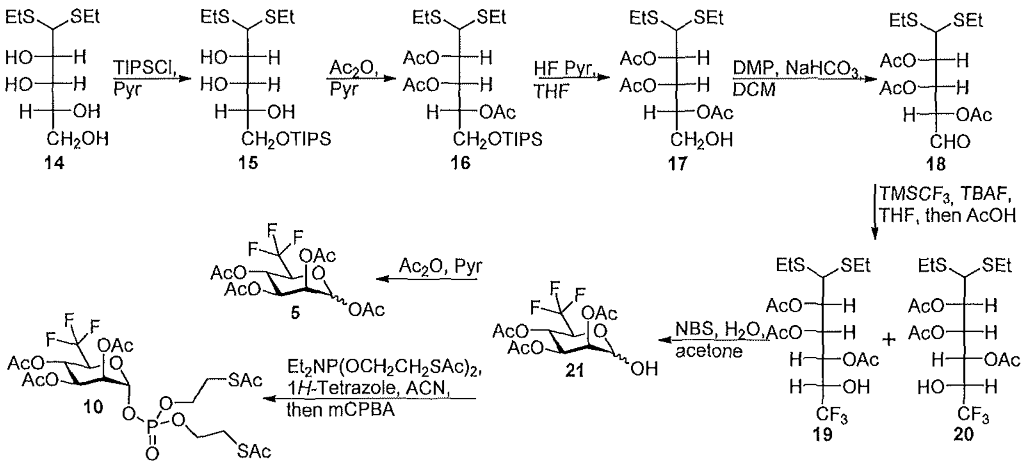
FIG. 3B: Synthetic route towards trifluoride analogs. Example for d-rhamnose analog 10.
Figure 3C:
FIG. 3C: Synthetic route towards phosphoramidite reagent.
Figure 3D:
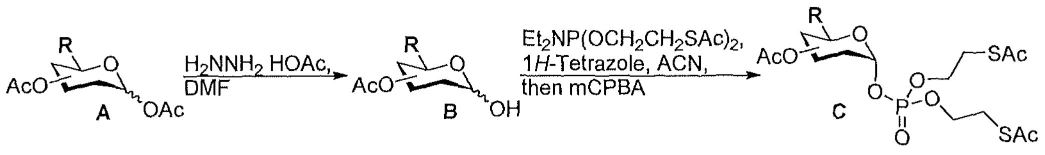
FIG. 3D: Overview of general procedures described in Example 1.

Ac, acetyl; ACN, Acetonitrile; AcOH Acetic acid; aq., aqueous; DCM dichloromethane; DMAP, dimethylaminopyridine; DMF, N,N-Dimethylformamide; DMP, Dess-Martin periodinane; EtOAc, ethyl acetate; eq., equivalent; Hept, heptane; hrs, hours; mCPBA, meta-chloroperoxybenzoic acid; min, minutes; NBS, N-bromosuccinimide; Pyr, pyridine; r.t., room temperature; sat., saturated; TBDMS, tert-Butyldiphenylsilyl; TEA, triethylamine; THF, tetrahydrofuran; TIPS, triisopropylsilyl; TMS, trimethylsilyl; Tol, toluene General Synthetic Procedures See FIG. 3D.

General Procedure A: Selective 1-Deacetylation

Compound A (1 eq.) was dissolved in DMF (0.3 M) and hydrazine acetate (1.2 eq.) was added at 0° C. After stirring for 5 minutes, the mixture was stirred till completion at r.t. which was typically after 3 hrs. The mixture was diluted with DCM, washed with sat. aq. $NaHCO_3$ and brine. The organic layer was dried over anhydrous $Na_2SO_4$, filtered concentrated in vacuo. The residue was purified by silicagel flash column chromatography (EtOAc in Hept) to afford compound B.

General Procedure B: 1-Phosphorylation

Similar as described previously (Yu, S.-H.; et al., PNAS 2012, 109 (13), 4834-4839), compound B (1 eq.) and di-(S-acetyl-2-thioethyl)-N,N-diethylphosphoroamidite (1.1 eq) were dissolved in in ACN (0.35 M) at 0° C. and 1H-tetrazole (1.4 eq, 0.45 M in acetonitrile) was slowly added. After full conversion, typically after 1 hr, mCPBA (2.4 eq, 77% wt.) was added at 0° C. and stirred for 30 min. The mixture was diluted with EtOAc and 10% aq. $Na_2SO_3$ and the organic layer was washed with sat. aq. $NaHCO_3$ and brine. The aqueous phases were extracted two more times with fresh EtOAc and the combined organic layers were dried over anhydrous $Na_2SO_4$, filtered concentrated in vacuo. The residue was purified by silicagel flash column chromatography (EtOAc in Hept) to afford compound C.

Synthetic Procedures for Compounds of the Invention and Intermediated Thereof

1

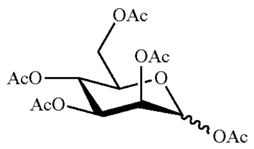

1,2,3,4,6-penta-O-acetyl-D-mannopyranoside (P-D-Man, 1). Synthesis was performed as described previously and the data is identical to the data previously reported.[3]. TLC: (60:40, EtOAc:Hept v/v) $R_f$=0.53. $^{1}H$ NMR (500 MHz, $CDCl_3$, major anomer) δ 6.09 (d, J=1.9 Hz, 1H, H1), 5.36-5.34 (m, 2H, H3 & H4), 5.27-5.26 (m, 1H, H2), 4.29 (dd, J=12.4, 4.8 Hz, 1H, H6a), 4.11 (dd, J=12.4, 2.5 Hz, 1H, H6b), 4.06 (dtd, J=6.2, 4.6, 2.5 Hz, 1H, H5), 2.18 (s, 3H, $CH_3$ Ac), 2.17 (s, 3H, $CH_3$ Ac), 2.10 (s, 3H, $CH_3$ Ac), 2.06 (s, 3H, $CH_3$ Ac), 2.01 (s, 3H, $CH_3$ Ac); $^{13}C$ NMR (126 MHz, $CDCl_3$, major anomer) δ 170.73 (CO Ac), 170.08 (CO Ac), 169.83 (CO Ac), 169.63 (CO Ac), 168.15 (CO Ac), 90.71 (C1), 70.72 (C5), 68.85 (C3), 68.45 (C2), 65.66 (C4), 62.21 (C6), 20.96 ($CH_3$ Ac), 20.87 ($CH_3$ Ac), 20.81 ($CH_3$ Ac), 20.76 ($CH_3$ Ac), 20.74 ($CH_3$ Ac); HRMS (m/z): $[M+Na]^+$ calcd for $C_{16}H_{22}NaO_{11}$, 413.10598; found, 413.10835.

2

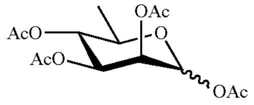

1,2,3,4-tetra-O-acetyl-D-rhamnopyranoside (P-D-Rha, 2). D-Rhamnose (230 mg; 1.52 mmol) was dissolved in pyridine (2.2 mL; 18 eq.) and acetic anhydride (1.7 mL; 12 eq.) was slowly added at 0° C. The mixture was stirred for 16 hrs while slowly warming to r.t. The mixture was concentrated in vacuo and the residue was dissolved in DCM, washed with aq. HCl (1 M), sat. aq. $NaHCO_3$ and brine. The organic layer was dried over anhydrous $MgSO_4$, filtered and concentrated in vacuo. The residue was purified by silicagel flash column chromatography (0%→20 EtOAc in Hept) to afford 2 (466 mg; 1.40 mmol; qu.). TLC: (50:50, EtOAc: Hept v/v) $R_f$=0.44. $^{1}H$ NMR (500 MHz, $CDCl_3$, major anomer) δ 6.02 (d, J=1.9 Hz, 1H, H1), 5.32-5.29 (m, 1H, H3), 5.25 (dd, J=3.5, 2.0 Hz, 1H, H2), 5.12 (t, J=10.0 Hz, 1H, H4), 3.94 (dq, J=9.8, 6.2 Hz, 1H, H5), 2.17 (s, 3H, $CH_3$ Ac), 2.16 (s, 3H, $CH_3$ Ac), 2.07 (s, 3H, $CH_3$ Ac), 2.01 (s, 3H, $CH_3$ Ac), 1.24 (d, J=6.2 Hz, 3H, 3×H6); $^{13}C$ NMR (126 MHz, $CDCl_3$, major anomer) δ 170.17 (CO Ac), 169.92 (CO Ac), 169.90 (CO Ac), 168.47 (CO Ac), 90.76 (C1), 70.59 (C4), 68.89 (C3), 68.83 (C5), 68.76 (C2), 21.02 ($CH_3$ Ac), 20.89 ($CH_3$ Ac), 20.87 ($CH_3$ Ac), 20.79 ($CH_3$ Ac), 17.56 (C6). HRMS (m/z): $[M+Na]^+$ calcd for $C_{14}H_{20}NaO_9$, 355.10050; found, 355.10295.

3

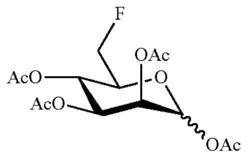

1,2,3,4-tetra-O-acetyl-6-fluoro-D-rhamnopyranoside (P-D-Rha6F, 3). Synthesis was performed as described previously and the data is identical to the data previously reported.[4] TLC: (60:40, EtOAc:Hept v/v) $R_f$=0.53. $^{1}$H NMR (500 MHz, $CDCl_3$, major anomer) δ 6.10 (d, J=1.9 Hz, 1H, H1), 5.39-5.36 (m, 2H, H3 & H4), 5.27 (td, J=2.2, 0.6 Hz, 1H, H2), 4.54-4.42 (m, 2H, H6a & H6b), 4.08-3.99 (m, 1H, H5), 2.18 (s, 3H, $CH_3$ Ac), 2.17 (s, 3H, $CH_3$ Ac), 2.08 (s, 3H, $CH_3$ Ac), 2.02 (s, 3H, $CH_3$ Ac); $^{13}$C NMR (126 MHz, $CDCl_3$, major anomer) δ 170.11 (CO Ac), 169.87 (CO Ac), 169.57 (CO Ac), 168.14 (CO Ac), 90.62 (C1), 81.29 (d, J=175.8 Hz, C6), 71.42 (d, J=19.5 Hz, C5), 68.78 (C3), 68.36 (C2), 65.24 (d, J=6.6 Hz, C4), 20.94 ($CH_3$ Ac), 20.83 ($CH_3$ Ac), 20.74 (2×$CH_3$ Ac); $^{19}$F NMR (470 MHz, $CDCl_3$, major anomer) δ −232.46 (td, J=47.1, 22.9 Hz, 6F). HRMS (m/z): $[M+Na]^+$ calcd for $C_{14}H_{19}FNaO_9$, 373.09108; found, 373.09255.

4

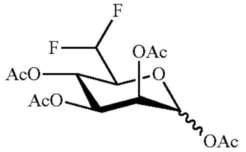

1,2,3,4-tetra-O-acetyl-6,6-difluoro-D-rhamnopyranoside (P-D-Rha6$F_2$, 4). Synthesis was performed as described previously.[5] TLC: (50:50, EtOAc:Hept v/v) $R_f$=0.55. HRMS (m/z): $[M+Na]^+$ calcd for $C_{14}H_{18}F_2NaO_9$, 391.08166; found, 391.08289. $^{1}$H NMR (500 MHz, $CDCl_3$) δ 6.12 (d, J=2.0 Hz, 1H, H1), 5.83 (td, J=54.2, 3.1 Hz, 1H, H6), 5.53 (t, J=10.0 Hz, 1H, H4), 5.37 (dd, J=10.0, 3.5 Hz, 1H, H3), 5.26 (dd, J=3.5, 2.0 Hz, 1H, H2), 4.04 (qd, J=9.9, 3.1 Hz, 1H, H5), 2.19 (s, 3H, $CH_3$ Ac), 2.18 (s, 3H, $CH_3$ Ac), 2.06 (s, 3H, $CH_3$ Ac), 2.02 (s, 3H, $CH_3$ Ac). $^{13}$C NMR (126 MHz, $CDCl_3$) δ 170.04 (CO Ac), 169.80 (CO Ac), 169.42 (CO Ac), 167.93 (CO Ac), 113.62 (t, J=245.6 Hz, C6), 90.27 (C1), 70.79 (t, J=24.3 Hz, C5), 68.28 (C3), 68.02 (C2), 63.97 (dd, J=3.7, 2.0 Hz, C4), 20.91 ($CH_3$ Ac), 20.82 ($CH_3$ Ac), 20.72 ($CH_3$ Ac), 20.67 ($CH_3$ Ac); $^{19}$F NMR (471 MHz, $CDCl_3$) δ −126.43 (ddd, J=295.5, 53.8, 9.4 Hz, 6Fa), −130.59 (ddd, J=295.6, 54.5, 11.2 Hz, 6Fb); HRMS (m/z): $[M+Na]^+$ calcd for $C_{14}H_{18}F_2NaO_9$, 391.08166; found, 391.08289.

5

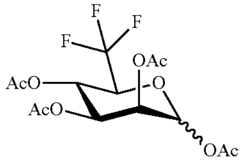

1,2,3,4-tetra-O-acetyl-6,6,6-trifluoro-D-rhamnopyranoside (P-D-Rha6$F_3$, 5). Compound 21 (40 mg; 0.12 mmol) was dissolved in pyridine (190 μL; 20 eq.) and acetic anhydride (110 μL; 10 eq.) was slowly added at 0° C. The mixture was then stirred for 4 hrs at r.t. The mixture was concentrated in vacuo and the residue was dissolved in DCM, washed with aq. HCl (1 M) and sat. aq. $NaHCO_3$. The organic layer was dried over anhydrous $MgSO_4$, filtered and concentrated in vacuo. The residue was purified by silicagel flash column chromatography (0%→30% EtOAc in Hept) to afford 5 (39.4 mg; 102 μmol; 88%). TLC: (50:50, EtOAc:Hept v/v) $R_f$=0.46. $^{1}$H-NMR (500 MHz, $CDCl_3$) δ 6.17 (d, J=2.0 Hz, 1H, H1), 5.59 (t, J=10.0 Hz, 1H, H4), 5.37 (dd, J=10.0, 3.4 Hz, 1H, H3), 5.26 (dd, J=3.4, 2.1 Hz, 1H, H2), 4.22 (dt, J=10.1, 5.6 Hz, 1H, H5), 2.20 (s, 3H, $CH_3$ Ac), 2.19 (s, 3H, $CH_3$ Ac), 2.06 (s, 3H, $CH_3$ Ac), 2.03 (s, 3H, $CH_3$ Ac). $^{13}$C-NMR (126 MHz, $CDCl_3$) δ 169.97 (CO Ac), 169.79 (CO Ac), 169.02 (CO Ac), 167.64 (CO Ac), 122.84 (q, J=280.8 Hz, C6), 90.16 (C1), 70.22 (q, J=31.5 Hz, C5), 68.09 (C3), 67.80 (C2), 63.71 (C4), 20.87 ($CH_3$ Ac), 20.81 ($CH_3$ Ac), 20.69 ($CH_3$ Ac), 20.58 ($CH_3$ Ac); $^{19}$F NMR (471 MHz, $CDCl_3$) δ −75.56 (d, J=5.8 Hz, $CF_3$); HRMS (m/z): $[M+Na]^+$ calcd for $C_{14}H_{17}F_3NaO_9$, 409.07224; found, 409.07328.

6

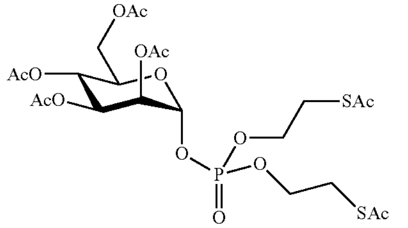

Di-(S-acetyl-2-thioethyl)-(2,3,4,6-tetra-O-acetyl-α-D-mannopyranoside) phosphate (P-D-Man-1P, 6). 2,3,4,6-tetra-O-acetyl-D-mannopyranoside[6] was reacted as described in general procedure B and purified by silicagel flash column chromatography (0%→50% EtOAc in Hept) affording 6 (61.6 mg; 97.4 μmol; 42%). TLC: before oxidation (80:20, EtOAc:Hept v/v) $R_f$=0.76 & after oxidation (80:20, EtOAc:Hept v/v) $R_f$=0.51. $^{1}$H NMR (500 MHz, $CDCl_3$) δ 5.65 (dd, J=6.5, 1.7 Hz, 1H, H1), 5.38-5.32 (m, 3H, H2 & H3 & H4), 4.31 (dd, J=12.4, 4.7 Hz, 1H, H6a), 4.24-4.16 (m, 5H, H5 & 2×$CH_2$—O), 4.14 (dd, J=12.4, 2.4 Hz, 1H, H6b), 3.20 (td, J=6.4, 4.7 Hz, 4H, 2×$CH_2$—S), 2.37 (s, 6H, 2×$CH_3$ SAc), 2.18 (s, 3H, $CH_3$ OAc), 2.11 (s, 3H, $CH_3$ OAc), 2.06 (s, 3H, $CH_3$ OAc), 2.00 (s, 3H, $CH_3$ OAc); $^{13}$C NMR (126 MHz, $CDCl_3$) δ 194.72 (CO SAc), 194.70 (CO SAc), 170.64 (CO OAc), 169.87 (CO OAc), 169.68 (CO OAc), 169.66 (CO OAc), 95.44 (d, J=5.4 Hz, C1), 70.59 (C5), 68.85 (d, J=10.9 Hz, C2), 68.34 (C3), 66.83-66.59 (m, 2×$CH_2$—O), 65.41 (C4), 62.13 (C6), 30.66 ($CH_3$ SAc), 30.64 ($CH_3$ SAc), 29.22 (d, J=7.3 Hz, 2×$CH_2$—S), 20.86 ($CH_3$ OAc), 20.83 ($CH_3$ OAc), 20.78 ($CH_3$ OAc), 20.72 ($CH_3$ OAc). $^{31}$P NMR (202 MHz, $CDCl_3$) δ −4.14 (1-OP); HRMS (m/z): $[M+Na]^+$ calcd for $C_{22}H_{33}NaO_{15}PS_2$, 655.08962; found, 655.08718.

7

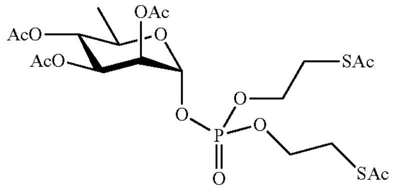

Di-(S-acetyl-2-thioethyl)-(2,3,4-tri-O-acetyl-α-D-rhamnopyranoside) phosphate (P-D-Rha-1P, 7). Compound 11 was reacted as described in general procedure B and purified by silicagel flash column chromatography (0%→50% EtOAc in Hept) affording 7 (234 mg; 407 μmol; 43%). TLC:

before oxidation (60:40, EtOAc:Hept v/v) $R_f$=0.61 & after oxidation (60:40, EtOAc:Hept v/v) $R_f$=0.25. $^1$H NMR (500 MHz, $CDCl_3$) δ 5.58 (dd, J=6.3, 1.9 Hz, 1H, H1), 5.34-5.29 (m, 2H, H2 & H3), 5.11 (t, J=10.0 Hz, 1H, H4), 4.23-4.05 (m, 5H, 2×$CH_2$—O & H5), 3.20 (td, J=6.4, 4.6 Hz, 4H, 2×$CH_2$—S), 2.37 (s, 6H, 2×$CH_3$ SAc), 2.16 (s, 3H, $CH_3$ OAc), 2.07 (s, 3H, $CH_3$ OAc), 1.99 (s, 3H, $CH_3$ OAc), 1.26 (d, J=6.2 Hz, 3H, 3×H6); $^{13}$C NMR (126 MHz, $CDCl_3$) δ 194.79 (CO SAc), 194.76 (CO SAc), 169.97 (2×CO OAc), 169.78 (CO OAc), 95.56 (d, J=5.3 Hz, C1), 70.35 (C4), 69.14 (d, J=11.0 Hz, C2), 68.73 (C5), 68.38 (C3), 66.72-66.48 (m, 2×$CH_2$—O), 30.66 (2×$CH_3$ SAc), 29.25 (d, J=7.4 Hz, 2×$CH_2$—S), 20.88 (2×$CH_3$ OAc), 20.77 ($CH_3$ OAc), 17.48 (C6); $^{31}$P NMR (202 MHz, $CDCl_3$) δ −3.97 (1-OP); HRMS (m/z): $[M+Na]^+$ calcd for $C_{20}H_{31}NaO_{13}PS_2$, 597.08414; found, 597.08291.

8

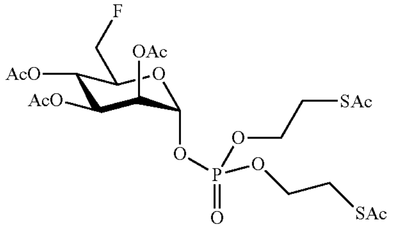

Di-(S-acetyl-2-thioethyl)-(2,3,4-tri-O-acetyl-6-fluoro-α-D-rhamnopyranoside) phosphate (P-D-Rha6F-1P, 8). Compound 12 was reacted as described in general procedure B and purified by silicagel flash column chromatography (0%→60% EtOAc in Hept) affording 8 (10.7 mg; 18.0 μmol; 19%). TLC: before oxidation (60:40, EtOAc:Hept v/v) $R_f$=0.61 & after oxidation (60:40, EtOAc:Hept v/v) $R_f$=0.34. $^1$H NMR (500 MHz, $CDCl_3$) δ 5.66 (dd, J=6.5, 1.8 Hz, 1H, H1), 5.40-5.32 (m, 3H, H2 & H3 & H4), 4.58-4.42 (m, 2H, H6a & H6b), 4.24-4.15 (m, 5H, H5 & 2×$CH_2$—O), 3.23-3.17 (m, 4H, 2×$CH_2$—S), 2.37 (s, 3H, $CH_3$ SAc), 2.36 (s, 2H, $CH_3$ SAc), 2.17 (s, 3H, $CH_3$ OAc), 2.08 (s, 3H, $CH_3$ OAc), 2.01 (s, 3H, $CH_3$ OAc); $^{13}$C NMR (126 MHz, $CDCl_3$) δ 194.79 (CO SAc), 194.78 (CO SAc), 169.92 (CO OAc), 169.75 (CO OAc), 169.65 (CO OAc), 95.39 (d, J=5.4 Hz, C1), 81.21 (d, J=176.0 Hz, C6), 71.31 (d, J=19.2 Hz, C5), 68.79 (d, J=11.2 Hz, C3), 68.31 (C2), 66.85-66.62 (m, 2×$CH_2$—O), 64.97 (d, J=6.7 Hz, C4), 30.66 (2×$CH_3$ SAc), 29.27-29.15 (m, 2×$CH_2$—S), 20.86 ($CH_3$ Ac), 20.79 ($CH_3$ Ac), 20.74 ($CH_3$ Ac); $^{31}$P NMR (202 MHz, $CDCl_3$) δ −4.05 (1-OP); $^{19}$F NMR (470 MHz, $CDCl_3$) δ −232.24 (td, J=47.2, 23.0 Hz, 6F); HRMS (m/z): $[M+Na]^+$ calcd for $C_{20}H_{30}FNaO_{13}PS_2$, 615.07472; found, 615.07346.

9

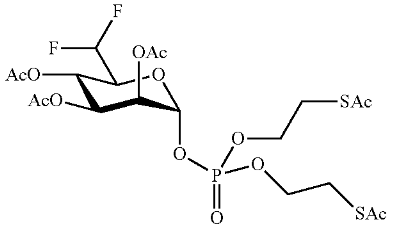

Di-(S-acetyl-2-thioethyl)-(2,3,4-tri-O-acetyl-6,6-difluoro-α-D-rhamnopyranoside) phosphate (P-D-Rha6$F_2$-1P, 9). Compound 13 was reacted as described in general procedure B and purified by silicagel flash column chromatography (0%→50% EtOAc in Hept) affording 9 (50.0 mg; 81.9 μmol; 32%). TLC: before oxidation (60:40, EtOAc:Hept v/v) $R_f$=0.65 & after oxidation (60:40, EtOAc:Hept v/v) $R_f$=0.42; $^1$H NMR (500 MHz, $CDCl_3$) δ 5.86 (td, J=54.0, 3.1 Hz, 1H, H6), 5.68 (dd, J=6.5, 2.0 Hz, 1H, H1), 5.50 (t, J=10.0 Hz, 1H, H4), 5.38 (dd, J=9.9, 3.4 Hz, 1H, H3), 5.34 (dd, J=3.5, 2.0 Hz, 1H, H2), 4.20 (dddd, J=14.4, 9.6, 5.5, 2.5 Hz, 5H, H5 & 2×$CH_2$—O), 3.20 (q, J=6.3 Hz, 4H, 2×$CH_2$—S), 2.37 (s, 3H, $CH_3$ SAc), 2.37 (s, 3H, $CH_3$ SAc), 2.17 (s, 3H, $CH_3$ OAc), 2.07 (s, 3H, $CH_3$ OAc), 2.01 (s, 3H, $CH_3$ OAc); $^{13}$C NMR (126 MHz, $CDCl_3$) δ 194.70 (CO SAc), 194.69 (CO SAc), 169.78 (CO OAc), 169.60 (CO OAc), 169.44 (CO OAc), 113.40 (t, J=245.7 Hz, C6), 94.95 (d, J=5.3 Hz, C1), 70.42 (t, J=23.9 Hz, C5), 68.39 (d, J=11.0 Hz, C2), 67.74 (C3), 66.90-66.69 (m, 2×$CH_2$—O), 63.87 (t, J=2.8 Hz, C4), 30.60 (2×$CH_3$ SAc), 29.18-29.08 (m, 2×$CH_2$—S), 20.76 ($CH_3$ OAc), 20.65 (2×$CH_3$ OAc); $^{19}$F NMR (471 MHz, $CDCl_3$) δ −127.31 (ddd, J=295.3, 53.9, 10.3 Hz, 6Fa), −130.57 (ddd, J=295.2, 54.3, 10.3 Hz, 6Fb); $^{31}$P NMR (202 MHz, $CDCl_3$) δ −4.05 (1OP); HRMS (m/z): $[M+Na]^+$ calcd for $C_{20}H_{29}F_2NaO_{13}PS_2$, 633.06529; found, 633.06322.

10

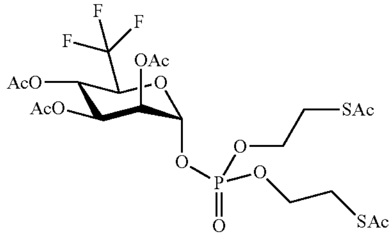

Di-(S-acetyl-2-thioethyl)-(2,3,4-tri-O-acetyl-6,6,6-trifluoro-α-D-mannopyranoside) phosphate (P-D-Rha6$F_{3-1}$P, 10). Compound 21 was reacted as described in general procedure B and purified by silicagel flash column chromatography (0%→40% EtOAc in Hept) affording 10 (95.0 mg; 151 μmol; 35%). TLC: before oxidation (60:40, EtOAc:Hept v/v) $R_f$=0.65 & after oxidation (60:40, EtOAc:Hept v/v) $R_f$=0.39; $^1$H-NMR (500 MHz, $CDCl_3$) δ 5.71 (dd, J=6.6, 1.9 Hz, 1H, H1), 5.58 (t, J=9.9 Hz, 1H, H4), 5.38 (dd, J=9.9, 3.4 Hz, 1H, H3), 5.35 (dd, J=3.4, 2.0 Hz, 1H, H2), 4.41 (dq, J=11.1, 5.6 Hz, 1H, H5), 4.27-4.14 (m, 4H, 2×$CH_2$—O), 3.22-3.17 (m, 4H, 2×$CH_2$—S), 2.37 (s, 3H, $CH_3$ SAc), 2.37 (s, 3H, $CH_3$ SAc), 2.19 (s, 3H, $CH_3$ OAc), 2.07 (s, 3H, $CH_3$ OAc), 2.02 (s, 3H, $CH_3$ OAc); $^{13}$C-NMR (126 MHz, $CDCl_3$) δ 194.68 (CO SAc), 194.65 (CO SAc), 169.71 (CO Ac), 169.60 (CO Ac), 169.03 (CO Ac), 122.84 (q, J=280.8 Hz, C6), 94.79 (d, J=5.3 Hz, C1), 69.81 (q, J=31.6 Hz, C5), 68.16 (d, J=11.0 Hz, C2), 67.54 (C3), 67.03-66.80 (m, 2×$CH_2$—O), 63.48 (C4), 30.61 ($CH_3$ SAc), 30.60 ($CH_3$ SAc), 29.19-29.05 (m, 2×$CH_2$—S), 20.75 ($CH_3$ OAc), 20.63 ($CH_3$ OAc), 20.55 ($CH_3$ OAc); $^{19}$F NMR (471 MHz, $CDCl_3$) δ −75.48 (d, J=5.7 Hz, $CF_3$); $^{31}$P NMR (202 MHz, $CDCl_3$) δ −4.05 (1-OP); HRMS (m/z): $[M+Na]^+$ calcd for $C_{20}H_{28}F_3NaO_{13}PS_2$, 651.05587; found, 651.05355.

11

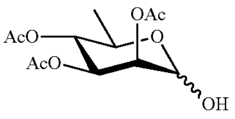

2,3,4-tri-O-acetyl-D-rhamnopyranoside (11). Compound 2 was reacted as described in general procedure A and purified by silicagel flash column chromatography (0%→50% EtOAc in Hept) affording 11 (323 mg; 1.11 mmol; 83%). TLC: (50:50, EtOAc:Hept v/v) $R_f$=0.33. $^1$H NMR (500 MHz, $CDCl_3$, major anomer) δ 5.37 (dd, J=10.1, 3.4 Hz, 1H, H3), 5.27 (dd, J=3.5, 1.8 Hz, 1H, H2), 5.17-5.15 (m, 1H, H1), 5.08 (t, J=10.0 Hz, 1H, H4), 4.17-4.10 (m, 1H, H5), 3.44 (d, J=3.7 Hz, 1H, 1OH), 2.16 (s, 3H, $CH_3$ Ac), 2.06 (s, 3H, $CH_3$ Ac), 2.00 (s, 3H, $CH_3$ Ac), 1.22 (d, J=6.3 Hz, 3H, 3×H6). $^{13}$C NMR (126 MHz, $CDCl_3$, major anomer) δ 170.45 (CO Ac), 170.30 (CO Ac), 170.26 (CO Ac), 92.23 (C1), 71.27 (C4), 70.43 (C2), 68.97 (C3), 66.50 (C5), 21.05 ($CH_3$ Ac), 20.94 ($CH_3$ Ac), 20.86 ($CH_3$ Ac), 17.59 (C6). HRMS (m/z): $[M+Na]^+$ calcd for $C_{12}H_{18}NaO_8$, 313.08994; found, 313.09287.

12

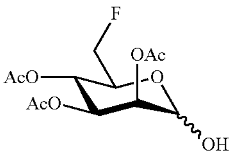

2,3,4-tri-O-acetyl-6-fluoro-D-rhamnopyranoside (12). Compound 3 was reacted as described in general procedure A and purified by silicagel flash column chromatography (0%→35% EtOAc in Hept) affording 12 (29.0 mg; 94.1 μmol; 66%). TLC: (60:40, EtOAc:Hept v/v) $R_f$=0.41. $^1$H NMR (500 MHz, $CDCl_3$, major anomer) δ 5.44 (dd, J=10.0, 3.3 Hz, 1H, H3), 5.31-5.27 (m, 2H, H4 & H2), 5.25 (d, J=1.8 Hz, 1H, H1), 4.54-4.42 (m, 2H, H6a & H6b), 4.24 (dddd, J=22.9, 10.3, 4.4, 2.8 Hz, 1H, H5), 3.96 (s, 1H, 1-OH), 2.16 (s, 3H, $CH_3$ Ac), 2.07 (s, 3H, $CH_3$ Ac), 2.01 (s, 3H, $CH_3$ Ac); $^{13}$C NMR (126 MHz, $CDCl_3$, major anomer) δ 170.47 (CO Ac), 170.30 (CO Ac), 170.03 (CO Ac), 92.24 (C1), 81.85 (d, J=174.2 Hz, C6), 70.11 (C2), 69.29 (d, J=19.0 Hz, C5), 68.90 (C3), 65.85 (d, J=7.0 Hz, C4), 21.00 ($CH_3$ Ac), 20.81 (2×$CH_3$ Ac); $^{19}$F NMR (470 MHz, $CDCl_3$, major anomer) δ −231.87 (td, J=47.2, 22.9 Hz, 6F); HRMS (m/z): $[M+Na]^+$ calcd for $C_{12}H_{17}FNaO_8$, 331.08051; found, 331.08349.

13

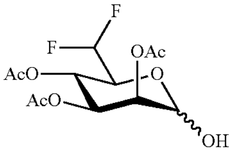

2,3,4-tri-O-acetyl-6,6-difluoro-D-rhamnopyranoside (13). Compound 4 was reacted as described in general procedure A and purified by silicagel flash column chromatography (0%→40% EtOAc in Hept) affording 13 (84.0 mg; 257 μmol; 83%). TLC: (60:40, EtOAc:Hept v/v) $R_f$=0.51. $^1$H-NMR (500 MHz, $CDCl_3$, major anomer) δ 5.83 (td, J=54.3, 3.2 Hz, 1H, H6), 5.47-5.40 (m, 2H, H4 & H3), 5.28-5.24 (m, 2H, H1 & H2), 4.65 (s, 1H, 1-OH), 4.24 (ddq, J=13.3, 6.3, 3.3 Hz, 1H, H5), 2.16 (s, 3H, $CH_3$ Ac), 2.06 (s, 3H, $CH_3$ Ac), 2.02 (s, 3H, $CH_3$ Ac); $^{13}$C-NMR (126 MHz, $CDCl_3$, major anomer) δ 170.55 (CO Ac), 170.43 (CO Ac), 170.04 (CO Ac), 114.05 (t, J=244.8 Hz, C6), 92.13 (C1), 69.85 (C2), 68.92-68.47 (m, C5 & C3), 64.84 (t, J=3.1 Hz, C4), 20.91 ($CH_3$ Ac), 20.74 ($CH_3$ Ac), 20.69 ($CH_3$ Ac); $^{19}$F NMR (471 MHz, $CDCl_3$, major anomer) δ −127.38 (ddd, J=293.8, 54.4, 11.4 Hz, 6Fa), −130.25 (ddd, J=293.7, 54.3, 10.1 Hz, 6Fb). HRMS (m/z): $[M+Na]^+$ calcd for $C_{12}H_{16}F_2NaO_8$, 349.07109; found, 349.07331.

14

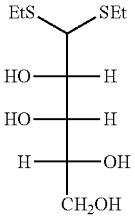

D-lyxose diethyl dithioacetal (14). D-Lyxose (6.00 g; 40.0 mmol) was dissolved in conc. HCl (27 mL, 1.5 M) and ethanethiol (6.3 mL; 81.9 mmol; 2.05 eq.; 97% wt.) was added dropwise at 0° C. After stirring for 27 hrs at 0° C. the mixture was extracted with EtOAc (4×) and the combined organic phases were neutralized by portion wise addition of solid $NaHCO_3$, dried over $Na_2SO_4$, filtered and concentrated in vacuo to afford 14 as white crystals (9.90 g; 38.6 mmol; 97%). TLC: (20:80, MeOH:DCM v/v) $R_f$=0.60. $^1$H NMR (500 MHz, $(CD_3)_2SO$)) δ 4.98 (d, J=6.1 Hz, 1H, 2-OH), 4.46 (t, J=5.6 Hz, 1H, 5-OH), 4.23 (d, J=8.2 Hz, 1H, 3-OH), 4.21 (d, J=1.5 Hz, 1H, H1), 4.17 (d, J=6.7 Hz, 1H, 4-OH), 3.84 (ddd, J=9.3, 6.1, 1.6 Hz, 1H, H2), 3.71 (d, J=6.8 Hz, 1H, H4), 3.54 (t, J=8.5 Hz, 1H, H3), 3.44-3.35 (m, 2H, 2×H5), 2.68-2.59 (m, 4H, 2×$CH_2$ SEt), 1.19 (dt, J=8.7, 7.4 Hz, 6H, 2×$CH_3$ SEt); $^{13}$C NMR (126 MHz, $(CD_3)_2SO$)) δ 73.85 (C2), 70.34 (C3), 69.56 (C4), 62.94 (C5), 54.98 (C1), 24.84 ($CH_2$ SEt), 24.67 ($CH_2$ SEt), 14.74 ($CH_3$ SEt), 14.71 ($CH_3$ SEt); HRMS (m/z): $[M+Na]^+$ calcd for $C_9H_{20}NaO_4S_2$, 279.07007; found, 279.07299.

15

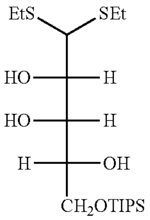

5-O-triisopropylsilyl-D-lyxose diethyl dithioacetal (15). Compound 14 (9.90 g; 38.6 mmol) and 4-dimethylamino-pyridine (472 mg; 3.86 mmol; 0.1 eq.) were dissolved in pyridine (110 mL; 0.35 M) and subsequently triisopropyl-silylchloride (9.3 mL; 42.5 mmol; 1.1 eq.; 97% wt.) was added dropwise at 0° C. After 48 hrs most of the starting material had converted and the mixture was concentrated in vacuo. The residue was dissolved in EtOAc, extracted with water, dried over $Na_2SO_4$, filtered and concentrated in vacuo. The residue was used for the next reaction without further purification. TLC: (50:50, EtOAc:Hept v/v) $R_f$=0.69; $^{1}$H NMR (500 MHz, $CDCl_3$) δ 4.23 (d, J=2.9 Hz, 1H, H1), 4.04 (q, J=5.3 Hz, 1H, H4), 3.97-3.88 (m, 4H, H2 & H3 & H5a & H5b), 3.12 (d, J=5.3 Hz, 1H, 3-OH), 2.90 (d, J=5.8 Hz, 1H, 4-OH), 2.87 (d, J=4.0 Hz, 1H, 2-OH), 2.74 (q, J=7.4 Hz, 2H, $CH_2$ SEt), 2.67 (q, J=7.4 Hz, 2H, $CH_2$ SEt), 1.29 (td, J=7.4, 3.8 Hz, 6H, 2×$CH_3$ SEt), 1.18-1.10 (m, 3H, 3×CH TIPS), 1.08 (d, J=6.5 Hz, 18H, 3×$CH_3$ TIPS); $^{13}$C NMR (126 MHz, $CDCl_3$) δ 73.30 (C2), 72.20 (C3), 69.67 (C4), 66.75 (C5), 54.84 (C1), 25.94 ($CH_2$ SEt), 25.82 ($CH_2$ SEt), 18.06 (3×$CH_3$ TIPS), 18.05 (3×$CH_3$ TIPS), 14.85 ($CH_3$ SEt), 14.69 ($CH_3$ SEt), 11.93 (3×CH TIPS). HRMS (m/z): $[M+Na]^+$ calcd for $C_{18}H_{40}NaO_4S_2Si$, 435.20350; found, 435.20401.

16

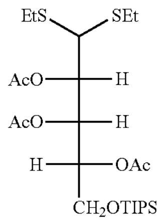

2,3,4-tri-O-acetyl-5-O-triisopropylsilyl-D-lyxose diethyl dithioacetal (16). Crude 15 was dissolved in pyridine (190 mL; 60 eq.) and acetic anhydride (109 mL; 30 eq.) was slowly added at 0° C. The mixture was stirred for 28 hrs while slowly warming to r.t. The mixture was concentrated in vacuo and the residue was dissolved in DCM, washed with aq. HCl (1 M), sat. aq. $NaHCO_3$ and brine. The organic layer was dried over anhydrous $MgSO_4$, filtered and concentrated in vacuo. The residue was purified by silicagel flash column chromatography (0%→10% EtOAc in Hept) to afford 16 (12.09 g; 22.444 mmol; 58% over 2 steps). TLC: (10:90, EtOAc:Hept v/v) $R_f$=0.24; $^{1}$H NMR (500 MHz, $CDCl_3$) δ 5.76 (dd, J=6.9, 1.8 Hz, 1H, H3), 5.39-5.33 (m, 2H, H2 & H4), 3.96 (d, J=5.4 Hz, 1H, H1), 3.74-3.64 (m, 2H, 2×H5), 2.76-2.59 (m, 4H, 2×$CH_2$ Et), 2.10 (s, 3H, $CH_3$ Ac), 2.08 (s, 3H, $CH_3$ Ac), 2.07 (s, 3H, $CH_3$ Ac), 1.25 (dt, J=8.4, 7.4 Hz, 6H, 2×$CH_3$ Et), 1.10-1.02 (m, 21H, 6×$CH_3$ TIPS & 3×CH TIPS); $^{13}$C NMR (126 MHz, $CDCl_3$) δ 170.36 (CO Ac), 169.87 (CO Ac), 169.74 (CO Ac), 71.65 (C2), 70.74 (C4), 70.26 (C3), 61.85 (C5), 51.76 (C1), 25.58 ($CH_2$ Et), 25.16 ($CH_2$ Et), 21.17 ($CH_3$ Ac), 20.92 (2×$CH_3$ Ac), 17.99 (6×$CH_3$ TIPS), 14.40 ($CH_3$ Et), 14.16 ($CH_3$ Et), 11.99 (3×CH TIPS); HRMS (m/z): $[M+Na]^+$ calcd for $C_{24}H_{46}NaO_7S_2Si$, 561.23519; found, 561.23388.

17

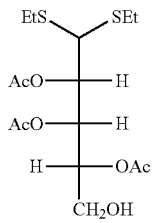

2,3,4-tri-O-acetyl-D-lyxose diethyl dithioacetal (17). Compound 16 (12.00 g; 22.27 mmol) was dissolved in THF (150 mL; 0.15 M) in a plastic bottle and hydrogen fluoride pyridine complex (15 mL; ~70%/30%) was added in portions over 3.5 hrs at 0° C. After stirring for an additional 14 hrs at r.t. all starting material was consumed and the mixture was diluted with EtOAc (100 mL) and carefully quenched with sat. aq. $NaHCO_3$. The organic layer was washed with 10% aq. $CuSO_4$ (2×) and the combined organic layers were dried over anhydrous $MgSO_4$, filtered and concentrated in vacuo. The residue was purified by silicagel flash column chromatography (0%→40% EtOAc in Hept) to afford 17 (4.85 g; 12.7 mmol; 57%). TLC: (40:60, EtOAc:Hept v/v) $R_f$=0.18. $^{1}$H NMR (400 MHz, $CDCl_3$) δ 5.59 (dd, J=8.8, 1.7 Hz, 1H, H3), 5.39 (dd, J=8.8, 3.5 Hz, 1H, H2), 5.06 (ddd, J=7.8, 6.2, 1.7 Hz, 1H, H4), 3.86 (d, J=3.5 Hz, 1H, H1), 3.53 (dt, J=12.0, 5.9 Hz, 1H, H5a), 3.38 (dd, J=11.7, 7.8 Hz, 1H, H5b), 2.80 (d, J=7.1 Hz, 1H, 5-OH), 2.71-2.52 (m, 4H, 2×$CH_2$ SEt), 2.11 (s, 3H, $CH_3$ Ac), 2.02 (s, 3H, $CH_3$ Ac), 2.01 (s, 3H, $CH_3$ Ac), 1.18 (td, J=7.4, 5.9 Hz, 6H, 2×$CH_3$ SEt); $^{13}$C-NMR (101 MHz, $CDCl_3$) δ 171.15 (CO Ac), 170.54 (CO Ac), 169.64 (CO Ac), 70.86 (C2), 70.62 (C4), 70.45 (C3), 60.05 (C5), 51.56 (C1), 25.81 ($CH_2$ SEt), 25.36 ($CH_2$ SEt), 20.93 ($CH_3$ Ac), 20.90 ($CH_3$ Ac), 20.70 ($CH_3$ Ac), 14.36 ($CH_3$ SEt), 14.15 ($CH_3$ SEt); HRMS (m/z): $[M+Na]^+$ calcd for $C_{15}H_{26}NaO_7S_2$, 405.10176; found, 405.10253.

18

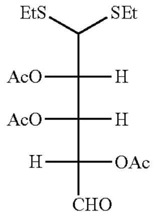

2,3,4-tri-O-acetyl-5-al-D-lyxose diethyl dithioacetal (18). Compound 17 (4.85 g; 12.7 mmol) was dissolved in dry DCM (106 mL; 0.12 M) and subsequently $NaHCO_3$ (10.7 g; 127 mmol; 10 eq.) and Dess-Martin periodinane (8.07 g; 19.0 mmol; 1.5 eq.) were added at 0° C. After 10 minutes the ice bath was removed and the mixture was stirred for an additional 3 hrs at r.t. The mixture was diluted with DCM (100 mL) and an aqueous solution (150 mL) of $Na_2SO_3$ (15 g) and $NaHCO_3$ (5 g) was added at 0° C. and stirred for 30 min. The organic phase was separated, dried over anhydrous $MgSO_4$, filtered and concentrated in vacuo. The residue was purified by silicagel flash column chromatography (0%→60% EtOAc in Hept) to afford 18 (3.65 g; 9.59 mmol; 76%) which was immediately used for the next step. TLC: (50:50, EtOAc:Hept v/v) $R_f$=0.32. HRMS (m/z): $[M+MeOH+Na]^+$ calcd for $C_{16}H_{28}NaO_8S_2$, 435.11233; found, 435.11239.

19

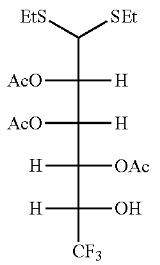

-continued

20

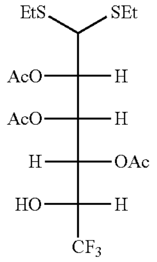

2,3,4-tri-O-acetyl-6,6,6-trifluoro-D-rhamnose diethyl dithioacetal (19) & 2,3,4-tri-O-acetyl-6,6,6-trifluoro-L-gulose diethyl dithioacetal (20). Synthetic procedure was adapted from a previously described procedure.[7] Compound 18 and trifluoromethyl(trimethyl)silane (1.45 mL; 9.56 mmol; 1.6 eq; 97% wt.) were dissolved in dry THF (20 mL; 0.3 M) and a tetrabutylammonium fluoride solution (598 μL; 598 μmol; 0.1 eq.; 1.0 M in THF) was added dropwise at 0° C. After stirring at 0° C. for 1.5 hrs the mixture was concentrated in vacuo. The residue was dissolved in $CHCl_3$, washed with water, dried over anhydrous $Na_2SO_4$, filtered and concentrated in vacuo. To remove the 5-OTMS groups, the residue was dissolved in 80% AcOH (0.25 M; 24 mL) and kept for 3 hrs at 50° C. The mixture was concentrated in vacuo and the residue was purified by silicagel flash column chromatography (0%→20%→30% EtOAc in Hept) to afford first 19 (813 mg; 1.80 mmol; 30%) and then 20 (816; 1.81 mmol; 30%). Compound 19: TLC: (30:70, EtOAc:Hept v/v) $R_f$=0.23. $^1$H-NMR (500 MHz, $CDCl_3$) δ 5.82 (dd, J=8.4, 1.3 Hz, 1H, H3), 5.48 (dd, J=9.5, 1.3 Hz, 1H, H4), 5.33 (dd, J=8.4, 4.2 Hz, 1H, H2), 3.97 (d, J=4.2 Hz, 1H, H1), 3.81 (dq, J=9.4, 6.3 Hz, 1H, H5), 2.77-2.60 (m, 5H, OH & 2×$CH_2$ SEt), 2.22 (s, 3H, $CH_3$ Ac), 2.10 (s, 3H, $CH_3$ Ac), 2.07 (s, 3H, $CH_3$ Ac), 1.26 (q, J=7.3 Hz, 7H, 2×$CH_3$ SEt); $^{13}$C-NMR (126 MHz, $CDCl_3$) δ 172.28 (CO), 169.85 (CO), 169.47 (CO), 124.34 (q, J=282.2 Hz, C6), 71.14 (C3), 71.06 (C2), 68.05-67.27 (m, C5&C4), 51.67 (C1), 26.06 ($CH_2$ SEt), 25.68 ($CH_2$ SEt), 21.22 ($CH_3$ Ac), 20.95 ($CH_3$ Ac), 20.68 ($CH_3$ Ac), 14.40 ($CH_3$ SEt), 14.26 ($CH_3$ SEt). $^{19}$F NMR (471 MHz, $CDCl_3$) δ −75.75 (d, J=6.4 Hz, $CF_3$); HRMS (m/z): $[M+Na]^+$ calcd for $C_{16}H_{25}F_3NaO_7S_2$, 473.08915; found, 473.08916. Compound 20: TLC: (30:70, EtOAc:Hept v/v) $R_f$=0.18. $^1$H-NMR (500 MHz, $CDCl_3$) δ 5.79 (dd, J=8.0, 2.5 Hz, 1H, H3), 5.60 (dd, J=2.5, 1.4 Hz, 1H, H4), 5.33 (dd, J=8.0, 4.2 Hz, 1H, H2), 4.29-4.21 (m, 1H, H5), 3.93 (d, J=4.2 Hz, 1H, H1), 2.79 (d, J=9.8 Hz, 1H, OH), 2.74-2.61 (m, 4H, 2×$CH_2$ SEt), 2.13 (s, 3H, $CH_3$ Ac), 2.13 (s, 3H, $CH_3$ Ac), 2.10 (s, 3H, $CH_3$ Ac), 1.25 (q, J=7.5 Hz, 7H, 2×$CH_3$ SEt); $^{13}$C-NMR (126 MHz, $CDCl_3$) δ 170.13 (CO), 169.94 (CO), 169.14 (CO), 123.68 (q, J=283.1 Hz, C6), 72.06 (C3), 71.20 (C2), 70.38 (q, J=31.4 Hz, C5), 65.43 (d, J=1.9 Hz, C4), 51.40 (C1), 25.86 ($CH_2$ SEt), 25.68 ($CH_2$ SEt), 21.07 ($CH_3$ Ac), 20.93 ($CH_3$ Ac), 20.68 ($CH_3$ Ac), 14.41 ($CH_3$ SEt), 14.21 ($CH_3$ SEt); $^{19}$F NMR (471 MHz, $CDCl_3$) δ −78.18 (d, J=6.8 Hz, $CF_3$); HRMS (m/z): $[M+Na]^+$ calcd for $C_{16}H_{25}F_3NaO_7S_2$, 473.08915; found, 473.08860.

21

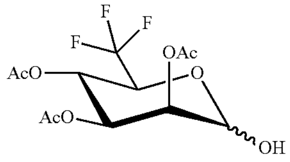

2,3,4-tri-O-acetyl-6,6,6-trifluoro-D-rhamnopyranoside (21). Compound 19 (763 mg; 1.69 mmol) was dissolved in a 5:1 acetone/water mixture (34 mL; 0.05 M) and NBS (1.51 g; 8.47 mmol; 5 eq.) was added at 0° C. After stirring for 45 min at 0° C., subsequently sat. aq. $NaHCO_3$ (15 mL) and sat. aq. $Na_2S_2O_3$ (15 mL) were added and the mixture was stirred for 15 min. The organic solvent was evaporated in vacuo and the remaining mixture was extracted with $Et_2O$ (2×), dried over anhydrous $MgSO_4$, filtered and concentrated in vacuo. The residue was purified by silicagel flash column chromatography (0%→30% EtOAc in Hept) to afford 21 (225 mg; 654 μmol; 39%). TLC: (50:50, EtOAc:Hept v/v) $R_f$=0.40; $^1$H-NMR (500 MHz, $CDCl_3$) δ 5.54 (t, J=9.9 Hz, 1H, H4), 5.44 (dd, J=10.0, 3.3 Hz, 1H, H3), 5.32 (s, 1H, H1), 5.26 (dd, J=3.3, 1.9 Hz, 1H, H2), 4.42 (dq, J=9.9, 5.9 Hz, 1H, H5), 4.20 (s, 1H, OH), 2.17 (s, 3H, $CH_3$ Ac), 2.06 (s, 3H, $CH_3$ Ac), 2.02 (s, 3H, $CH_3$ Ac); $^{13}$C-NMR (126 MHz, $CDCl_3$) δ 170.50 (CO Ac), 170.31 (CO Ac), 169.54 (CO Ac), 123.47 (q, J=280.4 Hz, C6), 92.26 (C1), 69.56 (C2), 68.71-67.90 (m, C5 & C3), 64.32 (C4), 20.93 ($CH_3$ Ac), 20.74 ($CH_3$ Ac), 20.62 ($CH_3$ Ac); $^{19}$F NMR (471 MHz, $CDCl_3$) δ −75.44 (d, J=6.0 Hz, 3×6F); HRMS (m/z): $[M+Na]^+$ calcd for $C_{12}H_{15}F_3NaO_8$, 367.06167; found, 367.06424.

22

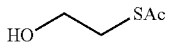

S-acetyl-2-thioethyl alcohol (22). Synthesis was performed as described previously and the data was identical.[8] TLC: (5:95, EtOAc:DCM v/v) $R_f$=0.15. $^1$H NMR (500 MHz, $CDCl_3$) δ 3.67 (t, J=6.3 Hz, 2H, $CH_2$—O), 3.01 (t, J=6.3 Hz, 2H, $CH_2$—S), 2.30 (s, 3H, $CH_3$ Ac); $^{13}$C NMR (126 MHz, $CDCl_3$) δ 196.42 (CO), 61.48 ($CH_2OH$), 31.89 ($CH_2$—S), 30.60 ($CH_3$ Ac)

23

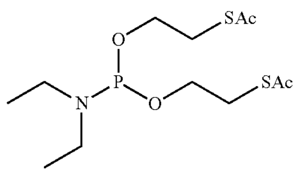

Di-(S-acetyl-2-thioethyl)-N,N-diethylphosphoroamidite (23). Compound 22 (5.88 g; 48.9 mmol; 2 eq.) was dissolved in anhydrous THF (31 mL; 1.6 M) and subsequently molecular sieves (4 Å) and anhydrous TEA (6.1 mL; 44.0 mmol; 1.8 eq.) were added. The mixture was cooled to 0° C., diethylphosphoramidous dichloride (3.56 mL; 24.5 mmol; 1 eq.). After stirring for 2 hrs the mixture was diluted with heptane, filtered and the filtrate was concentrated and directly purified by silicagel flash column chromatography (3% TEA in Hept) to afford 23 (3.90 g; 11.4 mmol; 47%).

The dry phosphoroamidite reagent was stored at −80° C. and after 11 months no changes in $^{1}H$ NMR were observed. TLC: (30:67:3, EtOAc:Hept:TEA v/v) $R_f$=0.53. $^{1}H$ NMR (500 MHz, $CDCl_3$) δ 3.73 (dddt, J=32.3, 10.7, 8.4, 6.5 Hz, 4H), 3.11 (t, J=6.6 Hz, 4H), 3.06 (dq, J=9.5, 7.1 Hz, 4H), 2.34 (s, 6H), 1.06 (t, J=7.1 Hz, 6H); $^{13}C$ NMR (126 MHz, $CDCl_3$) δ 195.08, 61.76 (d, J=16.0 Hz), 37.31 (d, J=20.7 Hz), 30.49, 30.37 (d, J=6.5 Hz), 14.98 (d, J=3.2 Hz); $^{31}P$ NMR (202 MHz, $CDCl_3$) δ 147.22 ($PNEt_2(OCH_2)_2$); HRMS (m/z): $[M+Na]^+$ calcd for $C_{12}H_{24}NNaO_5PS_2$, 380.07312; found, 380.07340.

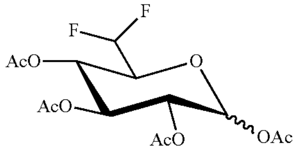

1,2,3,4-tetra-O-acetyl-6,6-difluoro-D-quinovopyranose (P-D-Qui6$F_2$, 24). Synthesis was performed as described previously. TLC: (80:20, EtOAc:Hept v/v) $R_f$=0.60. $^{1}H$ NMR (500 MHz, $CDCl_3$, major anomer) δ 6.37 (d, J=3.7 Hz, 1H, H1), 5.81 (td, J=54.1, 2.9 Hz, 1H, H6), 5.50 (dd, J=10.3, 9.3 Hz, 1H, H3), 5.31 (dd, J=10.3, 9.4 Hz, 1H, H4), 5.08 (dd, J=10.3, 3.6 Hz, 1H, H2), 4.13 (qd, J=10.0, 2.9 Hz, 1H, H5), 2.20 (s, 3H, $CH_3$ Ac), 2.05 (s, 3H, $CH_3$ Ac), 2.04 (s, 3H, $CH_3$ Ac), 2.02 (s, 3H, $CH_3$ Ac); $^{13}C$ NMR (126 MHz, $CDCl_3$, major anomer) δ 170.20 (CO), 169.64 (CO), 169.27 (CO), 168.56 (CO), 113.44 (t, J=245.6 Hz, C6), 88.65 (C1 alpha), 69.89 (dd, J=24.2 Hz, C5), 69.32 (C3), 68.90 (C2), 66.71 (dd, J=4.1, 1.8 Hz, C4), 20.84 ($CH_3$ Ac), 20.66 ($CH_3$ Ac), 20.50 ($CH_3$ Ac), 20.45 ($CH_3$ Ac); $^{19}F$ NMR (471 MHz, $CDCl_3$, major anomer) δ −127.11 (ddd, J=295.2, 53.7, 9.8 Hz, 6Fa), −131.09 (ddd, J=295.1, 54.4, 11.3 Hz, 6Fb).

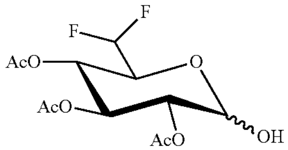

2,3,4-tri-O-acetyl-6,6-difluoro-D-quinovopyranose (P-D-Qui6$F_2$-1OH, 25). Compound 24 was reacted as described in general procedure A and purified by silicagel flash column chromatography (0%→30% EtOAc in Hept) affording 25 (25.0 mg; 76.6 μmol; 26%). TLC: (40:60, EtOAc:Hept v/v) $R_f$=0.25. $^{1}H$ NMR (500 MHz, $CDCl_3$, major anomer) δ 5.80 (td, J=54.2, 3.1 Hz, 1H, H6), 5.57 (dd, J=10.2, 9.3 Hz, 1H, H3), 5.52 (d, J=3.6 Hz, 1H, H1), 5.22 (dd, J=10.2, 9.3 Hz, 1H, H4), 4.88 (dd, J=10.3, 3.6 Hz, 1H, H2), 4.28 (qd, J=10.4, 3.2 Hz, 1H, H5), 3.72 (s, 1H, 1OH), 2.09 (s, 3H, $CH_3$ Ac), 2.04 (s, 3H, $CH_3$ Ac), 2.03 (s, 3H, $CH_3$ Ac); $^{13}C$ NMR (126 MHz, $CDCl_3$, major anomer) δ 170.35 (CO Ac), 170.33 (CO Ac), 169.74 (CO Ac), 113.92 (t, J=244.9 Hz, C6), 90.18 (C1), 70.87 (C2), 69.45 (C3), 67.83-67.41 (m, C4&C5), 20.79 ($CH_3$ Ac), 20.77 ($CH_3$ Ac), 20.63 ($CH_3$ Ac); $^{19}F$ NMR (471 MHz, $CDCl_3$, major anomer) δ −127.42 (ddd, J=293.9, 54.2, 11.4 Hz, 6Fa), −130.53 (ddd, J=293.9, 54.3, 10.1 Hz, 6Fb).

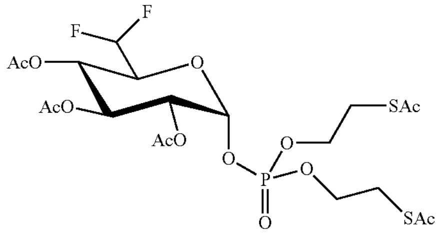

Di-(S-acetyl-2-thioethyl)-(2,3,4-tri-O-acetyl-6,6-difluoro-D-quinovopyranose) phosphate (P-D-Qui6$F_{2-1}$P, 26). Compound 25 was reacted as described in general procedure B and purified by silicagel flash column chromatography (0%→60% $Et_2O$ in Tol) affording 26 (6.2 mg; 10 μmol; 12%). TLC: before oxidation (40:60, EtOAc:Hept v/v) $R_f$=0.35 & after oxidation (60:40, $Et_2O$:Toluene v/v) $R_f$=0.24; $^{1}H$ NMR (500 MHz, $CDCl_3$) δ 5.89 (dd, J=6.9, 3.4 Hz, 1H, H1), 5.83 (td, J=54.0, 2.9 Hz, 1H, H6), 5.51 (t, J=9.8 Hz, 1H, H3), 5.31-5.29 (m, 1H, H4), 4.99 (ddd, J=10.2, 3.4, 2.6 Hz, 1H, H2), 4.29-4.11 (m, 5H, H5 & 2×$CH_2$—O), 3.25-3.14 (m, 4H, 2×$CH_2$—S), 2.37 (s, 3H, $CH_3$ SAc), 2.37 (s, 3H, $CH_3$ SAc), 2.09 (s, 3H, $CH_3$ OAc), 2.05 (s, 3H, $CH_3$ OAc), 2.03 (s, 3H, $CH_3$ OAc); $^{13}C$ NMR (126 MHz, $CDCl_3$) δ 194.80 (CO SAc), 194.79 (CO SAc), 170.06 (CO OAc), 169.78 (CO OAc), 169.37 (CO OAc), 113.32 (t, J=245.7 Hz, C6), 93.70 (d, J=5.2 Hz, C1), 69.74-69.32 (m, C5&C2), 68.89 (C3), 66.78 (d, J=5.7 Hz, $CH_2$—O), 66.66 (d, J=5.8 Hz, $CH_2$—O), 66.71-66.60 (m, C4), 30.68 ($CH_3$ SAc), 30.67 ($CH_3$ SAc), 29.20 (d, J=5.9 Hz, $CH_2$ SAc), 29.14 (d, J=6.0 Hz, $CH_2$ SAc), 20.73 ($CH_3$ OAc), 20.66 ($CH_3$ OAc), 20.59 ($CH_3$ OAc). $^{19}F$ NMR (471 MHz, $CDCl_3$) δ −127.58 (ddd, J=295.4, 53.6, 10.5 Hz, 6Fa), −130.94 (ddd, J=295.0, 54.3, 10.7 Hz, 6Fb). $^{31}P$ NMR (162 MHz, $CDCl_3$) δ −3.52 (1-OP)

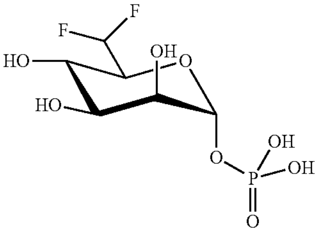

6,6-difluoro-α-D-rhamnopyranoside 1-phosphate (D-Rha6$F_{2-1}$P, 27). Compound 9 (9.8 mg; 16 μmol) was dissolved in dry MeOH (0.32 mL; 0.05 M) and a 5.4M solution of sodium methoxide in MeOH (6.8 μL; 37 μmol; 2.3 eq.) was added at 0° C. The mixture was stirred to r.t. overnight to completion. Dowex™ 50WX8 200-400 mesh ion-exchange resin was added, stirred for 10 minutes and the mixture was filtered and concentrated in vacuo. TLC: (3:1:0.1, ACN:$H_2O$:AcOH v/v) $R_f$=0.15.

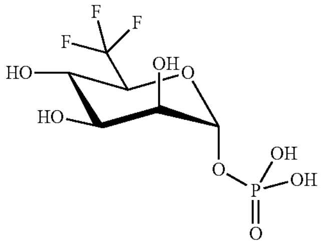

6,6,6-trifluoro-α-D-rhamnopyranoside 1-phosphate (D-Rha6$F_3$-1P, 28). Compound 10 (5 mg; 8 μmol) was dissolved in dry MeOH (0.2 mL; 0.05 M) and a 5.4M solution of sodium methoxide in MeOH (3 μL; 18 μmol; 2.3 eq.) was added at 0° C. The mixture was stirred to r.t. over 4 days to completion. Dowex™ 50WX8 200-400 mesh ion-exchange resin was added, stirred for 10 minutes and the mixture was filtered and concentrated in vacuo to afford 28. $^1$H NMR (500 MHz, $D_2O$) δ 5.49 (d, J=7.6 Hz, 1H, H1), 4.28 (dq, J=12.3, 6.2 Hz, 1H, H5), 4.04-4.03 (m, 1H, H2), 3.99-3.96 (m, 2H, H4 & H3); $^{13}$C NMR (126 MHz, $D_2O$) δ 127.33-120.43 (m, C6), 95.74 (d, J=5.7 Hz, C1), 70.59 (q, J=28.9 Hz, C5), 69.79 (C2), 69.13 (C3), 65.47 (C4); $^{19}$F NMR (471 MHz, $D_2O$) δ −74.14 (d, J=7.2 Hz, 3×6F); $^{31}$P NMR (202 MHz, $D_2O$) δ −2.45 (1-OP).

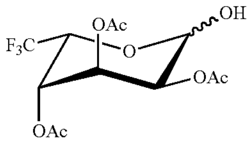

2,3,4-tri-O-acetyl-6,6,6-trifluoro-L-gulopyranoside (29). Compound 20 (1.0 g; 2.2 mmol) was dissolved in a 5:1 acetone/water mixture (53 mL; 0.05 M) and NBS (2.43 g; 13.7 mmol) was added at 0° C. After stirring for 50 min at 0° C., subsequently sat. aq. $NaHCO_3$ solution (15 mL) and sat. aq. $Na_2SO_3$ solution (15 mL) were added and the mixture was stirred for 30 min. The organic solvent was evaporated in vacuo and the remaining mixture was extracted with $Et_2O$ (2×), dried over anhydrous $MgSO_4$, filtered and concentrated in vacuo. The crude product was purified by silicagel flash column chromatography (0-30% EtOAc/heptane) to afford 29 (230 mg; 0.668 mmol; 30%). TLC: (50:50, EtOAc:Hept v/v) $R_f$=0.34; $^1$H NMR (400 MHz, $CDCl_3$) δ 5.41 (t, J=3.6 Hz, 1H, H3), 5.26 (dd, J=4.0, 1.6 Hz, 1H, H4), 5.10 (t, J=8.2 Hz, 1H, H1), 5.04 (dd, J=8.3, 3.2 Hz, 1H, H2), 4.37 (qd, J=6.3, 1.7 Hz, 1H, H5), 3.61 (d, J=8.0 Hz, 1H, OH), 2.17 (s, 6H, 2×$CH_3$ OAc), 2.07 (s, 3H, $CH_3$ OAc); $^{13}$C NMR (101 MHz, $CDCl_3$) δ 170.57 (C═O OAc), 168.98 (C═O OAc), 168.70 (C═O OAc), 124.60-120.55 (m, C6), 93.88 (C1), 71.44 (q, J=33.0 Hz, C5), 69.52 (C2), 67.61 (C3), 65.50 (C4), 20.81 ($CH_3$ OAc), 20.79 ($CH_3$ OAc), 20.74 ($CH_3$ OAc); $^{19}$F NMR (377 MHz, $CDCl_3$) δ −73.60 (d, J=6.3 Hz, $CF_3$).

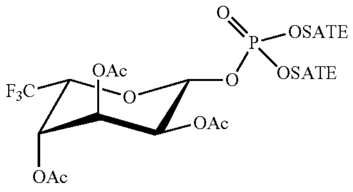

Di-(S-acetyl-2-thioethyl)-(2,3,4-tri-O-acetyl-6,6,6-trifluoro-L-gulopyranoside) phosphate (P-L-6d-Gul6$F_3$-1P, 30). A solution of 29 (209.5 mg; 0.609 mmol) and di-(S-acetyl-2-thioethyl)-N,N-diethylphosphoramidite (332.5 mg; 0.974 mmol) in anhydrous ACN (1.739 mL) was prepared at 0° C. 1H-tetrazole (1.893 mL; 0.45M in ACN) was added to the solution and the resulting reaction mixture was stirred for 1 h at 0° C. under $N_2$. The reaction mixture was concentrated in vacuo and the crude product was purified by flash column chromatography (0-40% EtOAc/heptane) to remove the excess of di-(S-acetyl-2-thioethyl)-N,N-diethylphosphoramidite. The crude product was redissolved in anhydrous ACN (1.739 mL) and mCPBA (323.8 mg; 1.445 mmol) was added at 0° C. The resulting reaction mixture was stirred for 40 min at 0° C. under $N_2$. Afterwards, the reaction mixture was diluted with EtOAc and 10% aq. $Na_2S_2O_3$ solution, and the organic layer was washed with sat. aq. $NaHCO_3$ solution and Brine. The aqueous phases were extracted two times with EtOAc and the combined organic layers were dried over anhydrous $MgSO_4$, filtered, and concentrated in vacuo. The crude product was purified by silicagel flash column chromatography (0-40% EtOAc/heptane), yielding 30 (208.6 mg; 0.332 mmol; 54%). TLC: (60:40, EtOAc:Hept v/v) $R_f$=0.39; $^1$H NMR (400 MHz, $CDCl_3$) δ 5.63 (dd, J=8.4, 7.2 Hz, 1H, H1), 5.46-5.42 (m, 1H, H3), 5.27 (dd, J=4.1, 1.6 Hz, 1H, H4), 5.14 (dd, J=8.3, 3.3 Hz, 1H, H2), 4.51-4.44 (m, 1H, H5), 4.23-4.07 (m, 4H, 2×$CH_2$—O), 3.22-3.12 (m, 4H, 2×$CH_2$—S), 2.35 (s, 6H, 2×$CH_3$ SAc), 2.17 (s, 3H, $CH_3$ OAc), 2.16 (s, 3H, $CH_3$ OAc), 2.04 (s, 3H, $CH_3$ OAc); $^{13}$C NMR (101 MHz, $CDCl_3$) δ 194.84 (C═O SAc), 194.75 (C═O SAc), 169.32 (C═O OAc), 168.83 (C═O OAc), 168.70 (C═O OAc), 94.96 (d, J=4.7 Hz, C1), 72.39-71.17 (m, C5), 67.76 (d, J=9.7 Hz, C2), 67.08 (C3), 66.70 (d, J=4.5 Hz, $CH_2$—O), 66.65 (d, J=4.2 Hz, $CH_2$—O), 65.15 (C4), 30.66 ($CH_3$ SAc), 30.63 ($CH_3$ SAc), 29.09 (d, J=1.4 Hz, $CH_2$—S), 29.01 (d, J=1.8 Hz, $CH_2$—S), 20.79 ($CH_3$ OAc), 20.72 ($CH_3$ OAc), 20.66 ($CH_3$ OAc); $^{19}$F NMR (377 MHz, $CDCl_3$) δ −73.53 (d, J=6.1 Hz, $CF_3$); $^{31}$P NMR (162 MHz, $CDCl_3$) δ −3.57 (q, J=7.9 Hz, 1-OP).

Example 2—Assay Conditions and Methods

Reagents

Biotinylated AAL, SNA, MAL-II, WGA, LCA, PSA, PNA, PHA-L and GSL-1 lectins and 10× Carbo-free Blocking Buffer were purchased from Vector laboratories Inc. Biotinylated AOL lectin was purchased from TCI Europe. 0.2 mg/ml Streptavidin-phycoerythrin conjugate was purchased from Fischer Scientific (Invitrogen, eBioscience). Unnatural sugar derivatives were synthesized as described under synthetic procedures and stored at −20° C. at a concentration of 100 mM/DMSO.

Cell Culture

THP-1 cells (TIB-202, ATCC) and Jurkat cells (TIB-152, ATCC) were cultured in RPMI-1640 medium containing 2 mM Glutamine and 25 mM HEPES (Gibco™, Life Technologies), supplemented with 10% v/v heat-inactivated fetal bovine serum (FBS) (Gibco™, Life Technologies) and 1× antibiotic-antimycotic solution (100 units/mL of penicillin, 100 μg/mL of streptomycin, and 0.25 μg/mL Fungizone) (Gibco™, Life Technologies) and passaged every 3-4 day by seeding a fraction of 0.5-2 min cells of the culture per 10 ml medium. EL-4 cells (TIB-39, ATCC) were cultured in DMEM medium (Gibco™, Life Technologies), supplemented with 10% v/v heat-inactivated fetal bovine serum (FBS) (Gibco™, Life Technologies), 1× antibiotic-antimycotic solution (100 units/mL of penicillin, 100 μg/mL of streptomycin, and 0.25 μg/mL Fungizone) (Gibco™, Life Technologies) and 2 mM Glutamine (Gibco™, Life Technologies) and passaged every 2-4 days by seeding a fraction of 0.5-1 min cells of the culture per 10 ml medium. For passaging a T75 flask (Corning), medium was removed and the monolayer was washed with 10 ml PBS pH 7.2 without $CaCl_2$) and $MgCl_2$ (Gibco™, Life Technologies) before adding 3.5 ml 0.05% trypsin/EDTA solution (Gibco™ 5 Life Technologies) in PBS. Cells were incubated at rt for 30-45 s after which the trypsin/EDTA-solution was removed. Cells were incubated for an additional 2 min at 37° C., 5.0% $CO_2$ and resuspended in cell culture medium. Cells were then seeded at ~40.000 cells/$cm^2$ in new culture flasks. All cells were cultured at 37° C., 5% $CO_2$ in a humidified incubator.

Lectin Staining

Protocol below was repeated until n>=3 for each compounds using cells at different passage numbers. Cells were cultured in medium containing different concentrations of unnatural sugar derivatives on either 24-wells plates (adherent cell lines; 80,000 cells per well) (Corning) or 96-wells plates (suspension cell lines; 13,000-20,000 cells per well) (Thermo Scientific). DMSO, at same dilution as the unnatural sugar derivative stock solutions, was used as a positive control for lectin staining; P-Fuc2F was used for all concentrations as negative control. Cells were incubated for three days at 37° C. and 5% $CO_2$ in a humidified incubator. Cells were harvested and washed with 100 μl 1×CF-blocking buffer (Vector Laboratories Inc.) containing 1 mM $CaCl_2$) and 1 mM $MgCl_2$. The cells were then resuspended in 50 μl 0.5 μg/ml of 0.5 ng/ml biotinylated lectin in 1× carbo-free blocking buffer and incubated at 4-8° C. for 45-60 min. Cells were washed with 3×100 μl PBA (PBS containing 1% v/v FBS and 0.1% w/w sodium azide), incubated with 40 μl 1 μg/ml Streptavidin-phycoerythrin conjugate (Invitrogen, eBioscience) in PBA for 10-15 min at 4-8° C. Cells were then washed again with 3×100 μl PBA, resuspended in PBA and fluorescence was measured with a flow cytometer (Beckman & Dickinson FACS-Calibur). Each replicate for each condition with >10,000 gated events. Data was processed using FlowJo (FlowJo LLC). Percentage of lectin binding was obtained by normalizing the MFI values to the MFI values of the respective DMSO control.

Lectin Specificity

Protocol below was repeated until n>=3 for each compounds using cells at different passage numbers. Culture medium was prepared in in 96-wells plates (Thermo Scientific). For every unnatural sugar derivative, 11 wells containing 100 μM of unnatural sugar derivatives and 11 wells containing 10 μM of the unnatural sugar derivatives were prepared. DMSO, at same dilution as the tested probes, was used as a positive control for lectin staining. THP-1 Cells were cultured in the plates (20,000 cells per well) and the cells were incubated for three days at 37° C. and 5% $CO_2$. Cells were harvested and washed with 100 μl 1×CF-blocking buffer (Vector Laboratories Inc.) containing 1 mM $CaCl_2$) and 1 mM $MgCl_2$. The cells were then resuspended in 50 μl 0.5 μg/ml of either 0.5 ng/ml biotinylated AAL, AOL, SNA, MAL-II, WGA, LCA, PSA, PNA, PHA-L or GSL-1 lectin in 1× carbo-free blocking buffer or with 50 μl of non-supplemented 1× carbo-free blocking buffer and incubated at 4-8° C. for 45-60 min. Cells were washed with 3×100 μl PBA (PBS containing 1% v/v FBS and 0.1% w/w sodium azide), incubated with 40 μl 1 μg/ml Streptavidin-phycoerythrin conjugate (Invitrogen, eBioscience) in PBA for 10-15 min at 4-8° C. Cells were then washed again with 3×100 μl PBA, resuspended in PBA and fluorescence was measured with a flow cytometer (Beckman & Dickinson FACS-Calibur). Each replicate for each condition with >10,000 gated events. Data was processed using FlowJo (FlowJo LLC). Percentage of lectin binding was obtained by normalizing the MFI values to the MFI values of the respective DMSO control.

Onset and Recovery of Inhibition

Cells were cultured in medium containing different concentrations of unnatural sugar derivatives on 96-wells plates (suspension cell lines; 13,000-20,000 cells per well) (Thermo Scientific). DMSO, at same dilution as the unnatural sugar derivative stock solutions, was used as a positive control for lectin staining; P-Fuc2F was used for all concentrations as negative control. Cells were incubated for eight days at 37° C. and 5% $CO_2$ in a humidified incubator. Medium was changed after three and six days of incubation with cell culture medium without unnatural sugar derivatives. Every day cells were harvested and washed with 100 μl 1× CF-blocking buffer (Vector Laboratories Inc.) containing 1 mM $CaCl_2$) and 1 mM $MgCl_2$. The cells were then resuspended in 50 μl 0.5 μg/ml of either 0.5 ng/ml biotinylated AAL, AOL, SNA, MAL-II, WGA, LCA, PSA, PNA, PHA-L or GSL-1 lectin in 1× carbo-free blocking buffer or with 50 μl of non-supplemented 1× carbo-free blocking buffer and incubated at 4-8° C. for 45-60 min. Cells were washed with 3×100 μl PBA (PBS containing 1% v/v FBS and 0.1% w/w sodium azide), incubated with 40 μl 1 μg/ml Streptavidin-phycoerythrin conjugate (Invitrogen, eBioscience) in PBA for 10-15 min at 4-8° C. Cells were then washed again with 3×100 μl PBA, resuspended in PBA and fluorescence was measured with a flow cytometer (Beckman & Dickinson FACS-Calibur). Each replicate for each condition with >10,000 gated events. Data was processed using FlowJo (FlowJo LLC). Percentage of lectin binding was obtained by normalizing the MFI values to the MFI values of the respective DMSO control.

Example 3—Results

3.1—Compounds of the Invention Inhibit Focus Expression $EC_{50}$ values in micromolar for fucose expression inhibition are shown in the table below. Three cell lines (THP-1, Jurkat, EL4) were cultured for 3 days with 0-512 μM compound. The cells were stained with two fucose specific lectins (AAL & AOL) and analysed by flow cytometry, presented as mean percentage lectin binding normalized to control (n=3).

The compounds were also found to have advantageous toxicity profiles.

TABLE 1

$EC_{50}$ values in micromolar for fucose expression inhibition

| | THP-1 | | Jurkat | | EL4 | |
|---|---|---|---|---|---|---|
| Compound | AAL | AOL | AAL | AOL | AAL | AOL |
| DMSO | NI | NI | NI | NI | NI | NI |
| P-D-Man-1P (6) | NI | NI | NI | NI | NI | NI |
| P-D-Rha-1P (7) | NI | 137 | NI | 153 | NI | NI |
| P-D-Rha6F-1P (8) | 267 | 84.4 | 174 | 345 | NI | NI |
| P-D-Rha6$F_2$-1P (9) | 1.97 | 5.26 | 5.93 | 4.10 | 14.2 | 38.2 |
| P-D-Rha6$F_3$-1P (10) | 0.608 | 0.454 | 27.7 | 12.8 | NI | NI |
| P-Fuc2Feq | 44.9 | 30.7 | 115 | 121 | NI | NI |

NI = no inhibition ($EC_{50}$ > 500 μM).

3.2—Compounds of the Invention are Selective 4,6-Dehydratase Inhibitors

Figure 4A:
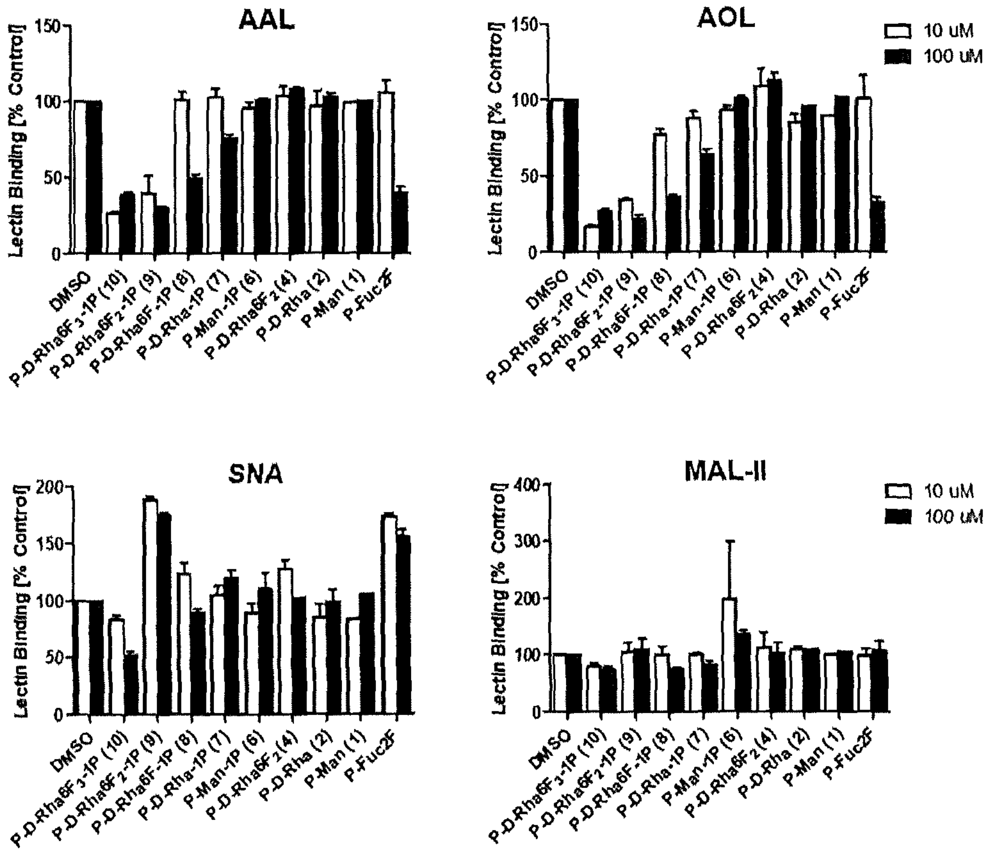
FIG. 4A: effect on total cell surface glycosylation evaluated using several lectins.
Figure 4B:
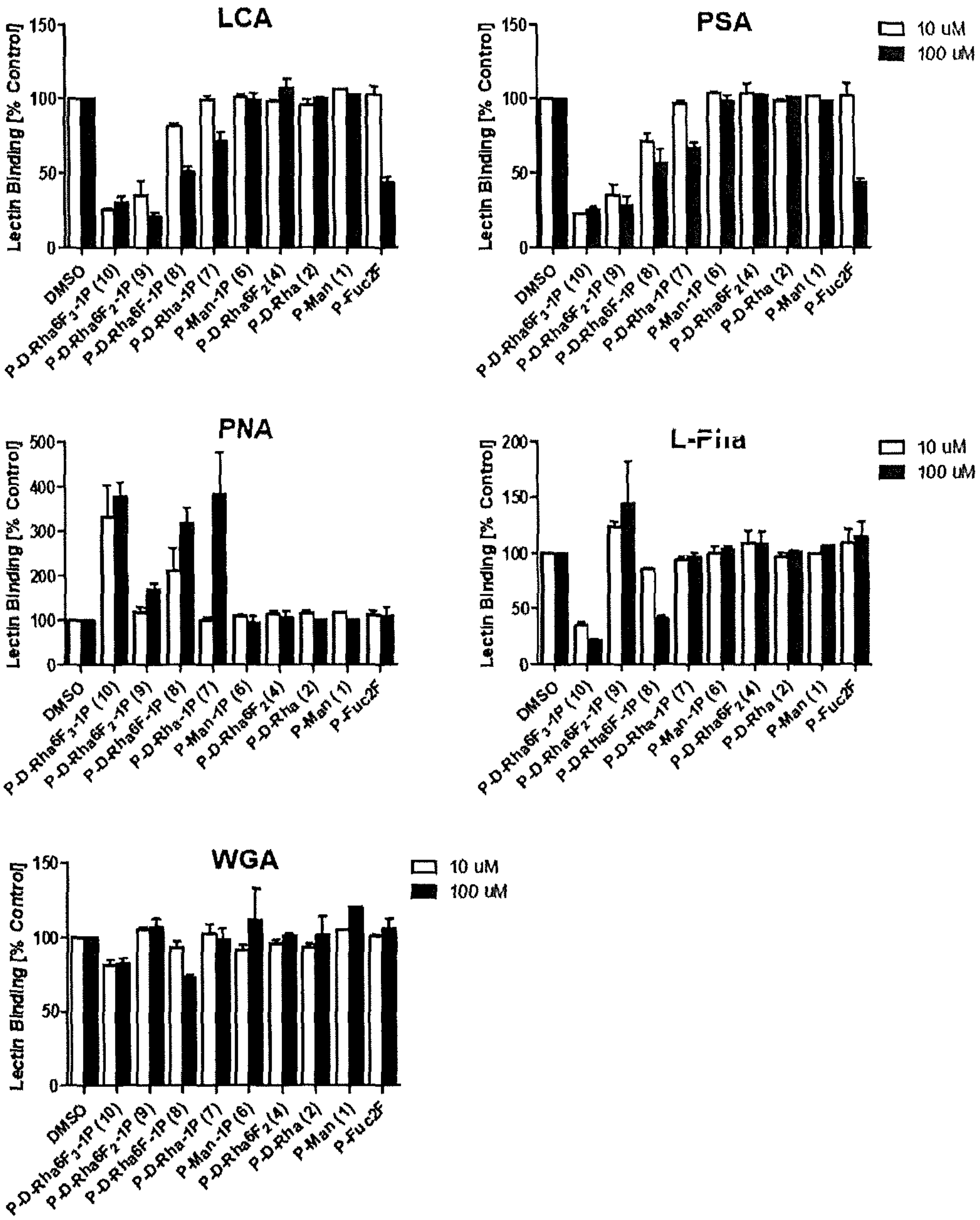
FIG. 4B: effect on total cell surface glycosylation evaluated using several lectins.

Compounds 9 & 10 are mannose-1-phosphate derivatives, so other glycosylation pathways such as mannosylation could be imagined to be affected. Having established the ability to inhibit cellular fucosylation with AAL and AOL lectins, the effect on total cell surface glycosylation was evaluated using additional lectins (FIG. 4A and FIG. 4B). N-glycans consist of a biantennary mannose containing backbone, recognized by WGA, and can be branched recognized by L-Pha. These branches can be terminated with galactose, recognized by PNA, or α2,6- and α2,3-linked sialic acids recognized by SNA and MAL-II, respectively. No significant effect on binding of these lectins was observed using 9 & 10. LCA and PSA did show decreased binding, however while they resemble the branching preference of WGA, their binding is restricted to N-glycans with α1,6-linked core fucosylation. The decrease in binding for these lectins can thus be attributed to defucosylation as confirmed by a decrease in AAL and AOL binding and no effect on WGA binding. Altogether this lectin screen shows that the compounds are specific for decreasing fucosylation and do not significantly alter mannosylation or other glycosylation pathways.

3.3—Compounds of the Invention are Potent 4,6-Dehydratase Inhibitors

Figure 5:
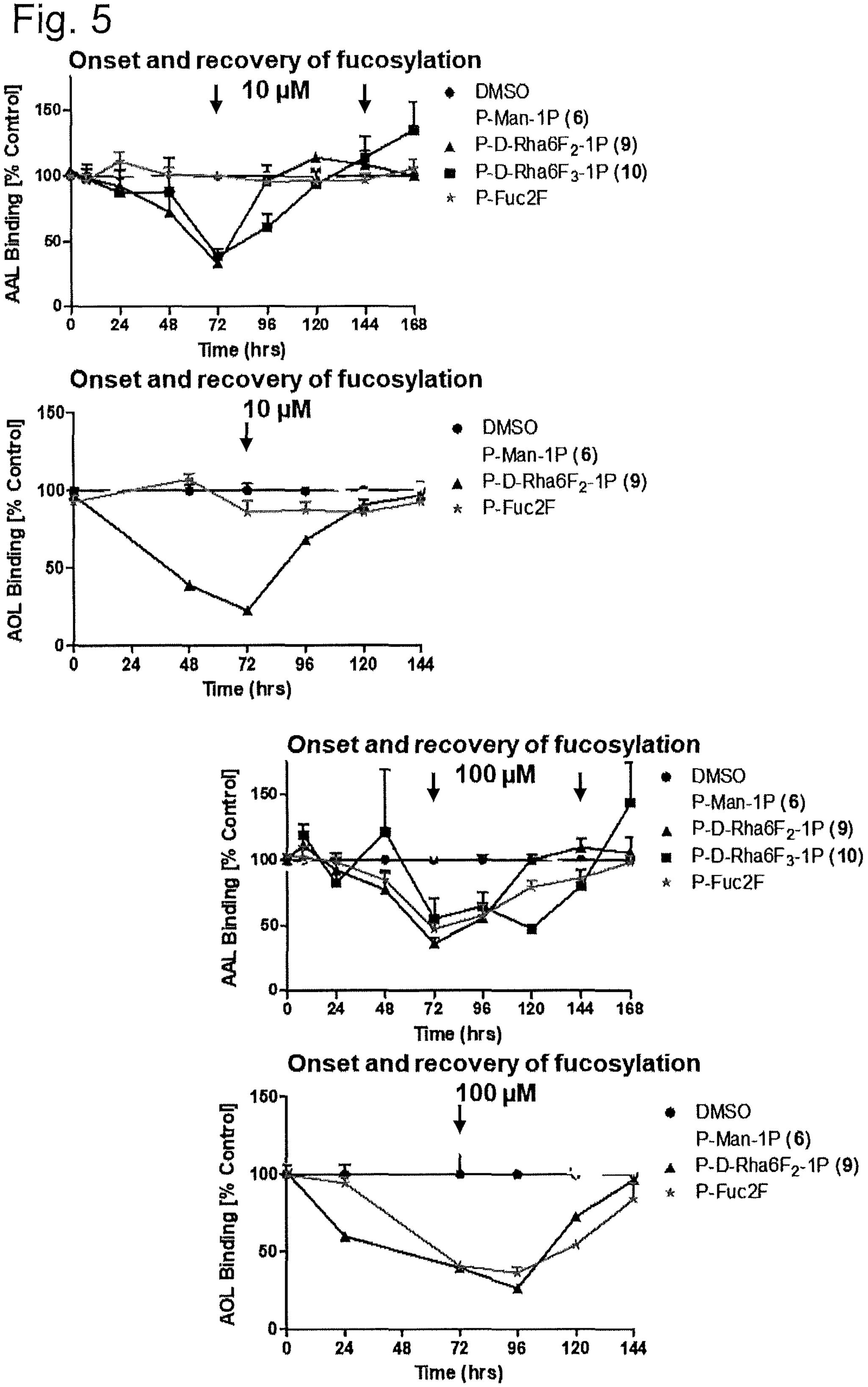
FIG. 5: evaluation of onset of inhibition and duration for recovery on THP-1 cells with 100 and 10 μM compound, using the AAL or AOL lectin as indicated. At 100 μM there is no effect for DMSO and P-Man-1P, while the other compounds reduce binding. At 10 μM the effect of P-Fuc2F is no longer discernible while compounds of the invention remain effective. Arrows indicate a change of culture medium without unnatural sugar derivatives.
Figure 6:
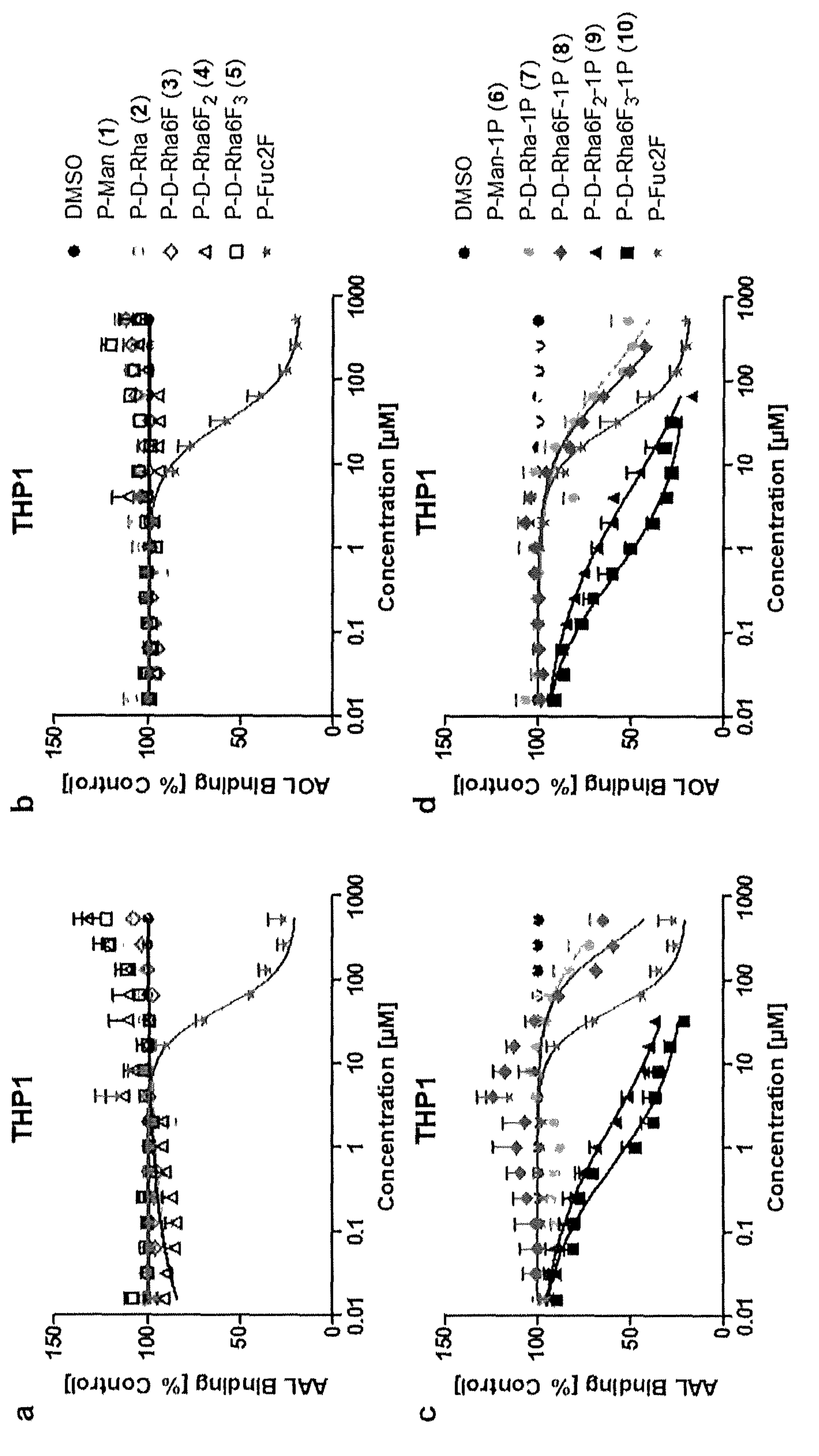
FIG. 6A: THP-1 cells were cultured for 3 days with 0-512 μM compound or DMSO control. The cells were stained with fucose specific lectin AAL and analysed by flow cytometry.
FIG. 6B: THP-1 cells were cultured for 3 days with 0-512 μM compound or DMSO control. The cells were stained with fucose specific lectin AOL and analysed by flow cytometry.
FIG. 6C: THP-1 cells were cultured for 3 days with 0-512 μM compound or DMSO control. The cells were stained with fucose specific lectin AAL and analysed by flow cytometry.
FIG. 6D: THP-1 cells were cultured for 3 days with 0-512 μM compound or DMSO control. The cells were stained with fucose specific lectin AOL and analysed by flow cytometry.
Figure 7:
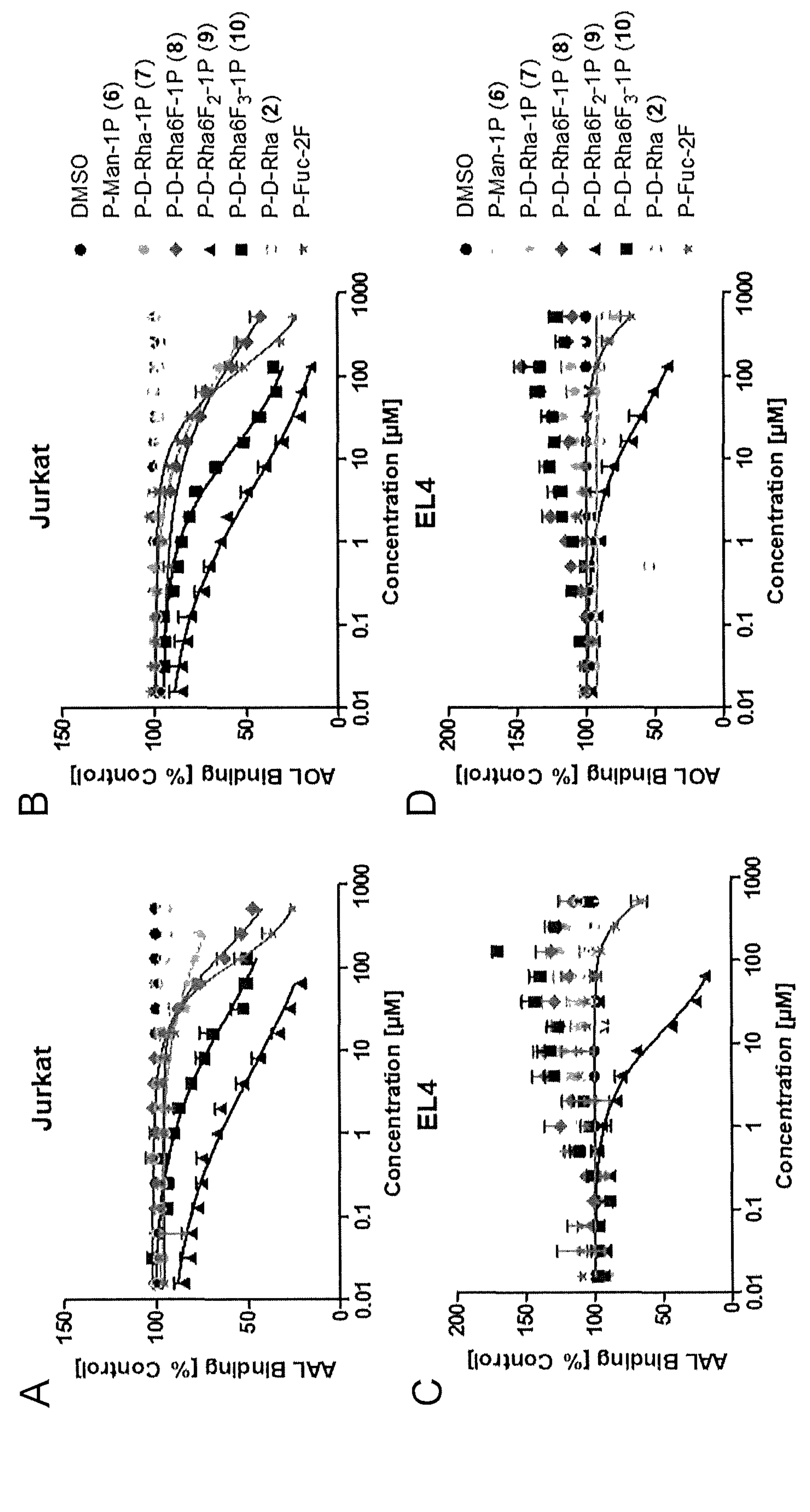
FIG. 7A: Jurkat cells were cultured for 3 days with 0-512 μM compound or DMSO control. The cells were stained with fucose specific lectin AAL and analysed by flow cytometry.
FIG. 7B: Jurkat cells were cultured for 3 days with 0-512 μM compound or DMSO control. The cells were stained with fucose specific lectin AOL and analysed by flow cytometry.
FIG. 7C: EL4 cells were cultured for 3 days with 0-512 μM compound or DMSO control. The cells were stained with fucose specific lectin AAL and analysed by flow cytometry.
FIG. 7D: EL4 cells were cultured for 3 days with 0-512 μM compound or DMSO control. The cells were stained with fucose specific lectin AOL and analysed by flow cytometry.

The onset of inhibition and duration for recovery was evaluated on THP-1 cells with 100 and 10 μM compound using the AAL lectin (FIG. 5). At 100 μM concentration compounds 9 and 10 inhibit fucosylation after 1 day and to over 50% after 3 days. Fucosylation was fully recovered to normal 5 levels on day 6. Strikingly, at 10 μM concentration no inhibition was observed for known inhibitor P-Fuc2F, while compounds of the invention decreased lectin binding to over 50% after 3 days with full recovery to normal fucosylation levels after 4-5 days (FIG. 5). Similar results were obtained using the AOL lectin.

3.4—Compounds of the Invention can be Covalent 4,6-Dehydratase Inhibitors

Having established the metabolism towards GDP-d-$Rha6F_2$ and GDP-d-$Rha6F_3$ inside the cell the inventors investigated the mechanism of inhibition using in silico experiments. It was assessed if the alterations on the C-6 position of GDP-mannose would be accepted by the GMDS enzyme. Initial substrate binding and the 4-keto analogs obtained after the first enzymatic step did not show altered binding. Without wishing to be bound to theory, it is thought that GDP-d-$Rha6F_2$ and GDP-d-$Rha6F_3$ can form a C5,6-unsaturated ketone, eliminating a fluoride, however after reduction by NADH a second fluoride can be eliminated. This reactive intermediate cannot be reduced due to the depletion of NADH so either competitively binds GMDS or eventually reacts with a nucleophilic amino acid in GMDS resulting in covalent inhibition or with water.

In conclusion, the inventors have developed de novo pathway dependent fucosylation inhibitors. They are potent, non-toxic, and specific for fucosylation, and can function via a new mechanism. They are therefore both tools to study fucosylation function and also suitable for further therapeutic development and applications.

The invention claimed is:

1. A compound of general formula (1-man) or (1-gal) or a salt thereof:

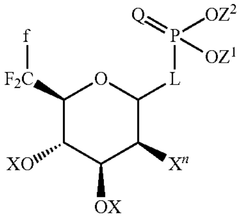
(1-man)

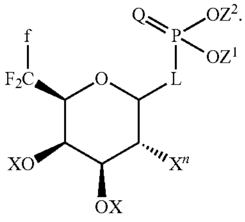
(1-gal)

wherein f is Hor F;

X is in each instance independently chosen from hydrogen and a linear, branched, or cyclic C1- 4acyl or alkyl wherein each carbon atom is optionally substituted by a halogen, an alkoxy, or a haloalkoxy moiety, and wherein the acyl or alkyl is optionally unsaturated;

X″ is —O—X, —$NH_2$, —NH—C1-4alkyl, —N(C1-4alkyl)$_2$, —NH—C1-4acyl, or —N(C1-4acyl)$_2$ wherein each carbon atom is optionally substituted by a halogen, an alkoxy, or a haloalkoxy moiety, and wherein the acyl or alkyl is optionally unsaturated;

L is O, S, NH, N($CH_3$), $CH_2$, CHF, or $CF_2$;

Q is O or S;

$Z^1$ and $Z^2$ are each independently chosen from hydrogen, benzyl or a linear, branched, or cyclic C1-6 acyl, alkyl, alkenyl, or alkynyl, wherein each carbon atom is optionally substituted by a halogen, an alkoxy, or a haloalkoxy moiety, a C1-4alkyl-Q'-C1-4acyl or a C1-4alkyl-Q'-C1-4alkyl, wherein each carbon atom is optionally substituted by a halogen, an alkoxy, or a haloalkoxy moiety, and wherein Q' is O or —O—C(═O)—O— or S or —S—S—, or $Z^1$ and $Z^2$ together form a C1-4alkyl bridging moiety that is optionally substituted with halogen or a C1-10hydrocarbon, or $Z^1$ is H and $Z^2$ together with the O to which it is attached form a nucleotide;

or $OZ^1$ is an N-linked amino acid.

2. The compound according to claim 1, wherein f is F; and/or

X is in each instance independently chosen from hydrogen and a linear C1-4acyl wherein each carbon atom is optionally substituted by a halogen or a methoxy moiety; and/or X″ is —O—X, —$NH_2$, or —NH—C1-4acyl; and/or L is O, S, NH, or $CF_2$; and/or Q is O; and/or $Z^1$ and $Z^2$ are each independently chosen from hydrogen, a linear C1-4alkyl, wherein each carbon atom is optionally substituted by a halogen, an alkoxy, or a haloalkoxy moiety, a C1-4alkyl-O—C1-4acyl, a C1-4alkyl-O—C1-4alkyl, a C1-4alkyl-S—C1-4acyl, or a C1-4alkyl-S—C1-4alkyl, wherein each carbon atom is optionally substituted by a halogen or a methoxy moiety, or $Z^1$ and $Z^2$ together form an optionally substituted C2-3alkyl bridging moiety, or $Z^1$ is H and $Z^2$ together with the O to which it is attached form a nucleotide.

3. The compound according to claim 1, wherein f is F.

4. The compound according to claims 1, wherein L is O.

5. The compound according to claim 1, wherein

X is in each instance chosen from acetyl, propionyl, and butyryl; and/or $Z^1$ is chosen from hydrogen, $-CH_2CH_2-$S-acetyl, and $-CH_2CH_2-$O-acetyl; and/or $Z^2$ is chosen from hydrogen, $-CH_2CH_2-$S-acetyl, and $-CH_2CH_2-$O-acetyl;

or $Z^1$ and $Z^2$ together form $-CH_2-CH_2-$ or $-CH_2-CH_2-CH_2-$ or $-CH_2-CH_2-$CH(C5-6aryl)-.

6. The compound according to claim 1, wherein $Z^1$ and $Z^2$ represent the same moiety.

7. The compound according to claim 1, wherein it is of general formula (1-man):

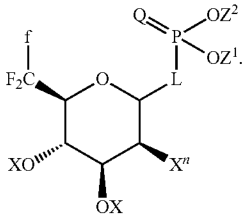

(1-man)

8. The compound according to claim 7, wherein f is F.

9. The compound according to claim 1, wherein the compound is selected from:

f=H, each X is H, X″ is OH, L is O, Q is O, $Z^1$ and $Z^2$ are $-CH_2CH_2-$S-acetyl;

f=F, each X is H, X″ is OH, L is O, Q is O, $Z^1$ and $Z^2$ are $-CH_2CH_2-$S-acetyl;

f=H, each X is acetyl, X″ is O-acetyl, L is O, Q is O, $Z^1$ and $Z^2$ are $-CH_2CH_2-$S-acetyl;

f=F, each X is acetyl, X″ is O-acetyl, L is O, Q is O, $Z^1$ and $Z^2$ are $-CH_2CH_2-$S-acetyl;

f=H, each X is H, X″ is OH, L is O, Q is O, $Z^1$ and $Z^2$ are H;

f=F, each X is H, X″ is OH, L is O, Q is O, $Z^1$ and $Z^2$ are H;

f=H, each X is acetyl, X″ is O-acetyl, L is O, Q is O, $Z^1$ and $Z^2$ are H;

f=F, each X is acetyl, X″ is O-acetyl, L is O, Q is O, $Z^1$ and $Z^2$ are H.

10. Method for inhibiting a hexose-4,6-dehydratase, the method comprising the step of contacting the hexose-4,6-dehydratase with a compound as defined in claims 1.

11. The method according to claim 10, wherein the hexose-4,6-dehydratase is CDP-glucose 4,6-dehydratase, dTDP-glucose 4,6-dehydratase, GDP-mannose 4,6-dehydratase, UDP-glucose 4,6-dehydratase, UDP-N-acetylglucosamine 4,6-dehydratase, or GDP-N-acetyl-D-glucosamine 4,6-dehydratase.

12. Method of treating or delaying cancer, tumor metastasis, inflammation, infections, or genetic disorders in a subject in need thereof, the method comprising the step of administering to the subject a compound as defined in claim 1.

13. The compound according to claim 4, wherein Q is O.

14. The compound according to claim 1, wherein

X is in each instance acetyl; and/or $Z^1$ is chosen from hydrogen, $-CH_2CH_2-$S-acetyl, and $-CH_2CH_2-$O-acetyl; and/or $Z^2$ is chosen from hydrogen, $-CH_2CH_2-$S-acetyl, and $-CH_2CH_2-$O-acetyl;

$Z^1$ and $Z^2$ together form $-CH_2-CH_2-$ or $-CH_2-CH_2-CH_2-$ or $-CH_2-CH_2-$CH(C5-6aryl)-.

15. The compound according to claim 1, wherein f is F; and

X is in each instance independently chosen from hydrogen and a linear C1-4acyl wherein each carbon atom is optionally substituted by a halogen or a methoxy moiety; and X″ is —O—X, $-NH_2$, —NH—C1-4alkyl; and L is O, S, NH, or $CF_2$; and Q is O; and $Z^1$ and $Z^2$ are each independently chosen from hydrogen, a linear C1-4alkyl, wherein each carbon atom is optionally substituted by a halogen, an alkoxy, or a haloalkoxy moiety, a C1-4alkyl-O—C1-4acyl, a C1-4alkyl-O—C1-4alkyl, a C1-4alkyl-S—C1-4acyl, or a C1-4alkyl-S—C1-4alkyl, wherein each carbon atom is optionally substituted by a halogen or a methoxy moiety, or $Z^1$ and $Z^2$ together form an optionally substituted C2-3alkyl bridging moiety, or $Z^1$ is H and $Z^2$ together with the O to which it is attached form a nucleotide.

* * * * *